(12) United States Patent
Kodadek

(10) Patent No.: US 7,018,801 B2
(45) Date of Patent: Mar. 28, 2006

(54) SELECTION OF PEPTIDES WITH ANTIBODY-LIKE PROPERTIES

(75) Inventor: Thomas J. Kodadek, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 459 days.

(21) Appl. No.: 09/780,575

(22) Filed: Feb. 9, 2001

(65) Prior Publication Data

US 2001/0029024 A1 Oct. 11, 2001

Related U.S. Application Data

(60) Provisional application No. 60/182,060, filed on Feb. 11, 2000.

(51) Int. Cl.
*G01N 33/53* (2006.01)

(52) U.S. Cl. .................................. 435/7.1; 436/501

(58) Field of Classification Search ................ 435/7.1; 436/501
See application file for complete search history.

(56) References Cited

U.S. PATENT DOCUMENTS 6,214,561 B1 * 4/2001 Peters et al. ................. 435/7.1
6,365,347 B1 * 4/2002 Murray et al. ................. 435/6
6,610,495 B1 * 8/2003 Watt et al. .................... 435/7.1

OTHER PUBLICATIONS

Dostmann et al., Pharmacol. Ther. vol. 82, No's 2-3, pp. 373-387 (1999).*
Lehninger, Biochemistry: The Molecular Basis of Cell Structure and Function (Worth Publishing: 1970) pp. 729-736.*
Borman, "Combinatorial chemistry",*Chem. & Eng. News*, 75:43-62, 1997.
Burger and Still,"Simple strucutral requirements for sequence-selective peptide receptors? Tripeptide binding by a podand ionophore", *J. Org. Chem.*, 62:4785-4790, 1997.
Burton,"Phage display", *Immunotechnology*, 1:87-94, 1995.
Cairns et al., "A novel bacterial vector system for monitoring protein-protein interactions in the cAMP-dependent protein kinase complex", *Gene*, 185:5-9, 1997.
Chen et al.,"Fluorescent, sequence-selective peptide detection by synthetic small molecules", *Science*, 279:851-853, 1998.
Cheng et al., "Sequence-selective peptide binding with peptido-A,B-trans-steroidal receptor selected from an encoded combinatorial receptor library".*J. Amer. Chem. Soc.*, 118:1813-1814, 1996.
Dinarello,"Interleukin-β, interleukin-18 and the interleukin-1β converting enzyme", *Ann. N.Y. Acad. Sci.*, 856-1-11, 1998.
Dong et al., "Molecular forceps from combinatorial libraries prevent the farnesylation of Ras by binding to its carboxyl terminus", *Chem. & Biol.*, 6:133-141, 1999.
Dove et al., "Conversion of the ω subunit of *Eschericia coli* RNA polymerase into a transcriptional activator or activation target," *Gene and Development*, 12:745-754, 1998.
Fairbrother et al., "Novel peptides selected to bind vascular endothelial growth factor target the receptor-binding site", *Biochemistry*, 37:17754-17764, 1998.
Fancy and Kodadek,"Chemistry for the analysis of protein-protein interactions: Rapid and efficient cross-linking triggered by long wavelength light," *Proc. Natl. Acad. Sci. USA*, 96:6020-6024, 1999.
Fields and Song,"A novel genetic system to detect protein-protein interactions," *Nature*, 340:245-246, 1989.
Fodor,"Light-directed, spatially addressable parallel chemical synthesis," *Science*, 251:767-773, 1991.
Griffiths and Duncan,"Strategies for selection of antibodies by phage display," *Curr. Opin. Biotechnol.*, 9:102-108, 1998.
Hajduk et al.,"Discovery of potent nonpeptide inhibitors of stromelysin using SAR by NMR," *J. Amer. Chem. Soc.*, 119:5818-5827, 1997.
Han and Kodadek,"Peptides selected to bind the Gal80 repressor are potent transcriptoinal activation domains in yeast," *J. Biol. Chem.*, 275:14979-14984, 2000.
Harland and Weintraub, "Translation of mRNA injected into *Xenopus* oocytes is specifically inhibited by antisense RNA," *J. Cell Biol.*, 101:1094-1099, 1985.

(Continued)

*Primary Examiner*—Bennett Celsa
(74) *Attorney, Agent, or Firm*—Fulbright & Jaworski

(57) ABSTRACT

The present invention provides a highly sensitive screening assay for the identification of peptide binding partners to virtually any peptide or polypeptide ligand. Utilizing an expression-repression readout system, the inventors have screened libraries of peptides and identified relatively small peptide molecules that bind to the provided target.

27 Claims, 9 Drawing Sheets

OTHER PUBLICATIONS

He et al., "Transformation of wheat (*Triticum aestivum* L.) through electroporation of protoplasts," *Plant Cell Reports*, 14:192-196, 1994.

Hossain and Schneider, "Sequence-selective evaluation of peptide side-chain interaction. New artificial receptors for selective recognition in water," *J. Amer. Chem. Soc.*, 120: 11208-11209, 1998.

Hu et al., "Sequence requirements for coiled-coils: Analysis with λ Repressor-GCN4 leucine zipper fusions," *Science*, 250:1400-1403, 1990.

Hu,"Repressor fusions as a tool to study protein-protein interactions," *Structure*, 3:431-433, 1995.

Jappelli and Brenner, "Interaction between cAMP-dependent protein kinase catalytic subunit and peptide inhibitors analyzed with λ Repressor fusions," *J. Mol. Biol.*, 259:575-578, 1996.

Kim et al.,"Photo-induced protein cross-linking mediated by palladium porphyrins," *J. Amer. Chem. Soc.*, 121:11896-11897, 1999.

Kodadek,"Protein microarrays: prospects and problems," *Chem. & Biol.*, 64:1-11, 2001.

Maly et al.,"Combinatorial target-guided ligand assembly: identification of potent subtype-selective c-Src inhibitors," *Proc. Natl. Acad. Sci. USA*, 97:2419-2424, 2000.

Mikolajczyk et al.,"High yield, site-specific coupling of N-terminally modified β-lactamase to a proteolytically-derived single-sulfhydryl murine fab," *Biooconj. Chem.*, 5:636-646, 1994.

O'Brian-Simpson,"Polymerization of unprotected synthetic peptides: A view towards synthetic peptide vaccines," *J. Amer. Chem. Soc.*, 119:1183-1188, 1997.

Park and Raines,"Genetic selection for dissociative inhibitors of designated protein-protein interactions," *Nature Biotechnol*, 18:847-851, 2000.

Rader and Barbas,"Phage display of combinatorial antibody libraries," *Curr. Opin. Biotechnol.*, 8:503-508, 1997.

Rose,"Natural peptides as building blocks for the synthesis of large protein-like molecules with hydrazone and oxime linkages," *Bioconj. Chem.*, 7:552-556, 1996.

Sasaki et al., "A new application of a peptide library to identify selective interaction between small peptides in an attempt to develop recognition molecules toward protein surfaces," *Tetrahedron Letters*, 37:85-88, 1996.

Schneider et al., "Scaffold-hopping: by topological pharmacophore search: a contribution to virtual screening," *Angew Chem Int Ed Engl.*, 38:2894-2896, 1999.

Shao et al., "Sequence-selective receptors of peptides. A simple molecular design for construction of large combinatorial libraries of receptors," *J. Org. Chem.*, 61: 6086-6087, 1996.

Shuker et al., "Discovering high-affinity ligands for proteins: SAR by NMR," *Science*, 274:531-1534, 1996.

Still, "Discovery of sequence-selective peptide binding by synthetic receptors using encoded combinatorial libraries," *Acc. Chem. Res.*, 29:155-163, 1996.

Xie et al., "Biochemical characterization of the TATA-binding Gal4 activation domain complex," *JBC*, 275:31914-31920, 2000.

Yang et al.,"Protein-peptide interactions analyzed with the yeast two-hybrid system," *Nucl. Acids Res.*, 23:1152-1156, 1995.

Zhang et al., "An inhibitor of sequence specific proteolysis that targets the substrate rather than the enzyme," *Chem. Biol.*, 8:391-397, 2001.

Zhang et al.,"Genetic selection of short peptides that support protein oligomerization in vivo. *Current Biol.*," 9:417-420, 1999.

Zhang,"Selection and practical applications of peptide-binding peptides," *Nature Biotechnol.*, 18:71-74, 2000.

Zhu,"A Cdc6 protein-binding peptide selected using a bacterial two-hybrid-like system is a cell cycle inhibitor," *J. Biol. Chem.*, 275:32098-32105, 2000.

* cited by examiner

GST - 13mer-containing extract

Wash. Elute with maltose. Analyze by SDS-PAGE.

13mer target: KPAKSARSVRSQR
27mer Library-encoded peptide:
THTTSQTTLRDPDVYAGARWVTWRVGA

SELECTION OF PEPTIDES WITH ANTIBODY-LIKE PROPERTIES

The present application claims priority to U.S. Provisional Patent Application Ser. No. 60/182,060, filed Feb. 11, 2000, the entire text of which is specifically incorporated by reference herein without disclaimer.

BACKGROUND OF THE INVENTION

A. Field of the Invention

The present invention relates generally to the fields of protein chemistry, biochemistry, organic chemistry and molecular biology. More particularly, it concerns a novel screen for identifying peptides having target binding affinity.

B. Description of Related Art

With the end of the human genome project in sight, the next great challenge in human biology will be to deduce the function of the thousands of new gene products identified by the sequencing effort. Perhaps the most direct way to take advantage of knowing the sequences of these proteins would be to design compounds capable of binding specific epitopes in a factor of interest. These binding agents could then be used for a variety of purposes, including affinity purification of the protein or the manipulation of its post-translational modification (see below).

Unfortunately, peptides, or peptide epitopes in proteins, are difficult targets for molecular recognition studies in aqueous solution. An unstructured peptide, or even one with a well-defined secondary structure, does not present to a prospective ligand the kind of molecular crevices and canyons present in a typical globular protein or in a double helical nucleic acid, which shield interacting groups from competition by solvent water. Indeed, looking at the prior art, it was not clear that it would be possible to form stable, highly specific, non-covalent complexes between peptide targets and small molecules in water. Leucine zipper domains are the smallest known naturally occurring motif that supports sequence-specific interactions, and these moieties are comprised of 30 or more amino acids (Landschulz et al., 1990; O'Shea et al., 1992) there are no natural examples of short peptide sequences that are independently capable of mediating protein-protein interactions.

There has been considerable interest in the organic chemistry community in developing synthetic peptide receptors. While some elegant chemistry has been performed, the receptors that have evolved from these efforts are far from being practically useful to biologists. Still and co-workers searched synthetic combinatorial libraries of cyclic amides for molecules able to bind tripeptides and incorporated these into fluorescence-based sensor systems (Burger and Still, 1997; Chen et al., 1998; Cheng et al., 1996; Shao and Still, 1996; Still, 1996). Complexes with $K_D$s of 20–40 µM were obtained, but these receptors and the target peptides only associated in chloroform. The literature on receptor-peptide binding in water is even less developed. For example, Hossain & Schneider (Hossain and Schneider, 1998) describe tripartite receptors for di- and tripeptides comprised of a crown ether and a quaternary amine separated by a hydrophobic spacer. These bind hydrophobic di- and tripeptides in water with $K_D$s in the mM to µM range, and very modest sequence specificity. These receptors were designed specifically to utilize the charged N- and C-terminal ends of a small peptide in binding, and so would not be applicable to the recognition of peptide epitopes in proteins.

The only report in the literature of peptide-like epitope-binding molecules that function in water is that of Nestler and co-workers at Cold Spring Harbor (Dong et al., 1999). These workers employed synthetic, bead-bound libraries of "forcep" molecules as potential epitope receptors. These forceps were comprised of multiple copies of a single peptide or peptide-like molecule displayed on either a stiff or floppy molecular scaffold. Forceps that bind an epitope from Ras were isolated and shown to be able to inhibit the farnesylation of Ras when present at high concentrations. However, the Nestler study was restricted to these homo-oligomeric forceps, which bind their target weakly. It was not demonstrated that this is a system of general utility, nor was it demonstrated that simple epitope-binding peptides lacking an elaborate superstructure could be isolated. Finally, the method employed by Nestler and co-workers requires a synthetic target molecule.

At present, the only class of molecules generally useful for peptide recognition in water is antibodies. Antibodies are, of course, proteins; not low molecular weight compounds. They are relatively fragile compared to small molecules. Using classical methods, they are tedious and expensive to obtain, particularly in large quantities, although advances in the construction of single chain antibody libraries on phage (Griffiths and Duncan, 1998; Rader and Barbas, 1997) promise to speed up this process. Finally, antibodies are not easily rendered cell-permeable.

Another major issue with antibodies is one of scale. For example, immunoaffinity purification of multi-protein complexes containing an epitope-tagged protein is an important tool in probing the biochemistry of splicing, transcription, DNA replication and many other critical cellular processes. However, they are extremely expensive to carry out on a large scale since the commercially available monoclonal antibodies used for these studies sell for more than $100 per milligram. Furthermore, the antibody-epitope interaction is generally so tight, that yields of only 1–10% are realized when one attempts to elute the tagged complex from the column with synthetic epitope peptide. This also makes reuse of the resin very difficult. This technology is good enough to provide quantities sufficient for identification of the component polypeptides by microsequencing techniques, but it is difficult to prepare enough material for extensive biochemical analysis, let alone structural studies. Thus, a major goal in the proteomics area is to develop synthetic epitope receptors that function in water and bind their targets selectively with modest to very high affinities.

In order to achieve all the goals necessary for such projections, the following attributes are required of the desired affinity reagent. First, the epitope-binding molecule (EBM) must bind to a given epitope (sequence of about 5–15 amino acids) in a protein of interest with very high specificity. Furthermore, it is critical that the inventor is able to choose the epitope. Screens carried out using intact recombinant protein targets almost invariably identify molecules that recognize natural interaction sites, probably because these represent the most "bindable" surface of a protein (Fairbrother et al., 1998; Zhu et al., 2000). However, the inventor wishes to isolate native complexes where these interaction surfaces will generally be occupied, so the affinity reagent must recognize some other surface of the protein target.

Second, EBMs of both moderate and high affinity must be available. High affinity EBMs will be of utility in the construction of biosensors (Kodadek, 2001) and in other applications as antibody replacements. However, for the affinity purification of a protein and its associated factors, EBMs of modest affinity will be much more useful, since the target protein can be eluted much more efficiently from a modest affinity EBM under native conditions than from a tight-binding antibody. Based on data that will be discussed below, the inventors believe that for affinity chromatography applications, a $K_D$ between $10^{-4}$ M and $10^{-7}$ M would be ideal (Zhang et al., 2000). For biosensor applications, EBM-protein complexes with $K_D$s of $10^{-9}$ M or below are desired.

Third, the EBM must be a relatively small molecule that can be synthesized in at least milligram, and preferably gram, quantities. Fourth, the screen used to identify the EBM must be relatively rapid and convenient, so as to be capable of supporting high-throughput. Thus, it is clear that there remains a considerable need in the field for a reagent with all of foregoing properties.

SUMMARY OF THE INVENTION

Thus, in accordance with the present invention, there is provided a method for identifying a peptide-peptide interaction comprising (a) providing a first fusion construct comprising target peptide fused to a first DNA binding domain; (b) providing a second fusion construct comprising a library encoded peptide (LEP) fused to second DNA binding domain (DBD), wherein said second DBD works as a complex with said first DBD to facilitate binding of said complex to a prokaryotic operator region; (c) contacting said first and second fusion constructs in a prokaryotic host cell which comprises said prokaryotic operator region, wherein said prokaryotic operator region is operationally linked to a coding region for one or more indicator polypeptides; and (d) determining binding of said complex to said operator region, whereby binding of said complex to said operator region identifies said LEP as a binding partner for said target peptide.

The binding of the complex to the operator, in one embodiment, acts blocks the transcription of said coding region, for example, to render said prokaryotic host cell insensitive to phage infection. In this embodiment, step (d) may comprise infection with a phage that infects, replicates and lyses said prokaryotic host cell. For example, the operator may be the lacZ operator, and the first and second DBDs are derived from the λ repressor.

The one or more indicator polypeptides may produce a calorimetric or fluorescent product, or be an enzyme like β-gal. The target peptide may be 5 to about 5000 residues in length, or 10 to about 2000 residues in length. The LEP may be 5 to about 50 residues. The first and second fusion constructs may be encoded by a nucleic acid segment under the control of a promoter operable in said prokaryotic host cell.

The target peptide and LEP may bind with an affinity in the range of about $10^{-3}$ to about $10^{-6}$ M, in particular with an affinity in the range of about $10^{-4}$ M, about $10^{-5}$ M, or about $10^{-6}$ M.

The method may further comprise random mutagenesis of said LEP, followed by measuring the change, if any, in the binding affinity of said LEP for said target. The method may also comprise measuring binding of said LEP to the target peptide under a second set of more stringent conditions.

The method may further comprise (e) linking the identified LEP to a third peptide, whereby linking permits said identified LEP and the third peptide to interact independently with the target peptide; (f) then contacting the target peptide with the identified LEP-third peptide complex, and (g) followed by determining the change, if any, in the binding affinity of said LEP for the target peptide. Again, the measuring may also comprise measuring binding of said LEP to the target peptide under a second set of more stringent conditions.

The third peptide may be known to bind said target peptide, may be a member of a peptide or peptidomimetic library, may be an enzyme substrate, an antigen, or a eukaryotic cell antigen. For example, the enzyme substrate may be a bacterial, viral or fungal antigen. The eukaryotic cell antigen may be a tumor cell marker, an HLA antigen, a cell surface receptor, or a cell surface transporter.

In another embodiment, the method comprises, prior to the determining, the step of stabilizing the interaction between the target peptide and said LEP, for example, by cross-linking or phototrapping. The first peptide also may comprise a multimer of a smaller peptide unit.

The method may further comprise assessing binding of the target peptide to said identified LEP by Western blot, mass spectroscopy, or nuclear magnetic resonance.

In another embodiment, there is provided a method for screening a peptide library for peptide-peptide interactions comprising (a) providing a plurality of a first fusion construct comprising a target peptide fused to a first DNA binding domain; (b) providing a plurality of second fusion construct comprising a library of encoded peptide (LEPs) fused to second DNA binding domain (DBD), wherein the second DBD works as a complex with the first DBD to facilitate binding of the complex to a prokaryotic operator region; (c) transferring said pluralities of first and second fusion constructs into a prokaryotic host cell which comprises said prokaryotic operator region, wherein said prokaryotic operator region is operationally linked to a coding region for one or more indicator polypeptides; and (d) determining binding of complexes to the operator region, whereby binding of the complexes to the operator region identifies associated LEPs as binding partners for the target peptide. Steps (a)–(d) may be repeated at least once using the LEP identified in step (d). The LEPs, in one embodiment, may be synthesized from a four base cutter-digested DNA library. The method may also further comprise the step of sequencing a DNA encoding an identified LEP.

In still another embodiment, there is provided a library encoded peptide (LEP) selected according to a method comprising (a) providing a first fusion construct comprising target peptide fused to a first DNA binding domain; (b) providing a second fusion construct comprising the LEP fused to second DNA binding domain (DBD), wherein the second DBD works as a complex with the first DBD to facilitate binding of the complex to a prokaryotic operator region; (c) contacting the first and second fusion constructs in a prokaryotic host cell comprising said prokaryotic operator region, wherein the prokaryotic operator regions is operationally linked to a coding region for one or more indicator polypeptides; and (d) determining binding of the complex to the operator region, whereby binding of the complex to the operator region identifies the LEP as a binding partner for the target peptide.

In yet a further embodiment, there is provided a heterodimeric binding molecule comprising (a) a first peptide that binds to a target molecule; (b) a second peptide that binds to said target molecule, wherein at least one of said first and second peptides is a member of a peptide library; and (c) a linker molecule connecting said first and second peptides such that the linking permits said first and second peptides to interact independently with said target molecule. The binding molecule may further comprise a moiety that permits recovery of said molecule, for example, a magnetic bead. The heterodimeric binding molecule may be expressed on the surface of a phage.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

As shown in FIG. 1B., cells that contain library-encoded peptides (LEPs) that bind the target epitope, reconstitute the otherwise weak DNA-binding activity of the lambda Repressor DBD. This renders these cells immune to phage lambda infection, allowing them to be selected form the population.

DESCRIPTION OF ILLUSTRATIVE EMBODIMENTS

Figure 1A:
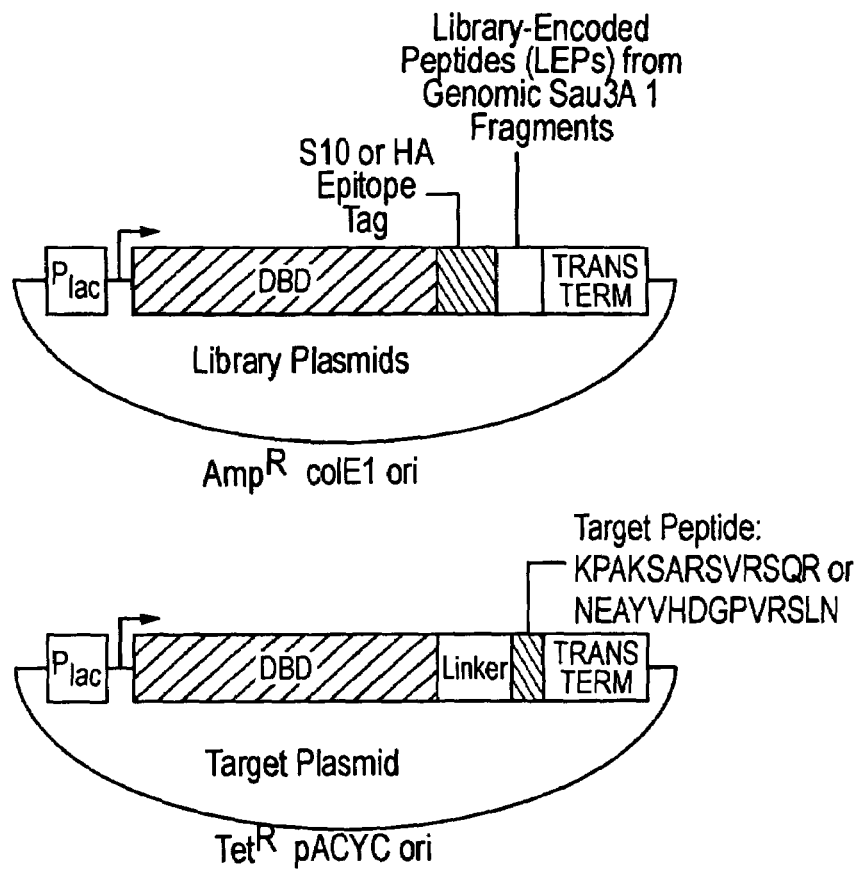
FIGS. 1A and 1B—Schematic representation of the screening protocol. The assay is carried out as described in Zhang et al. (Zhang et al. 2000). Two plasmids, depicted graphically in FIG. 1A., are transformed into E. coli. one encodes the lambda repressor DNA-binding domain (DBD) fused to a target epitope (SEQ ID NO:5 AND SEQ ID NO:3). The other encodes the DBD fused to a peptide library.

As discussed, an important goal in chemical biology is to be able to obtain specific ligands for any biomolecule of interest. Impressive advances have been made in isolating molecules, many of which are antibodies or antibody-derived, that bind proteins and nucleic acid targets with well-defined macromolecular structures. However, the identification of sequence-specific, peptide-binding ligands has been more difficult. In addition, even antibodies have major drawbacks: they are tedious and expensive to generate, difficult to produce in large quantities, are relatively fragile molecules unsuitable for certain field applications, and often bind so tightly that they or their target proteins are damaged upon attempted extraction. Natural peptide-binding proteins or protein domains have been mutagenized to derive species with novel binding specificities (Schneider et al., 1999), but like antibodies, these are globular macromolecules. Thus, though the development of synthetic receptor molecules has seen important advances in the last few years, the field remains in its infancy. Therefore, it remains an important goal to develop non-macromolecular species that retain the favorable molecular recognition characteristics of antibodies, but can be identified quickly and easily and synthesized in large amounts.

A. The Present Invention

It is envisioned that if it is possible to isolate small peptides that recognize specific epitopes within a target protein, then these reagents could be employed as capture ligands for that protein. This would obviate the need to create epitope-tagged versions of the native proteins for the purpose of immunoaffinity chromatography, a tedious and imperfect process that is not well-suited for high-throughput proteomic applications. An additional attraction of this approach to protein isolation would be that many proteins would co-purify with associated partners that could be identified by mass spectrometry techniques. This would provide an appealing alternative to the two-hybrid assay as a method to identify the binding partners of a given protein of interest. Finally, as will be described in detail, epitope-binding compounds have exciting potential as reagents for controlling the post-translational modification of proteins in a novel fashion. For example, an epitope-binding compound capable of recognizing a site of proteolysis or phosphorylation on a target protein could protect that factor from chemical modification. This would be an extremely valuable tool for molecular biology researchers and could also serve as the paradigm of a new family of therapeutic compounds.

The overall goal of this project was to develop a general method for the discovery of relatively low molecular weight EBMs that can be chemically synthesized (i.e., they are not macromolecules such as antibodies, other types of proteins, or nucleic acids). Thus, the inventor initiated an effort to isolate heteromeric complexes comprised of small peptides, even smaller than leucine zippers, that could be employed as EBMs. As stated above, a priori, it was not clear how feasible this endeavor would be. Stable, specific complexes between naturally-occurring peptides of less than 25–30 residues are essentially unknown, although complexes between small peptides and large proteins are very common. This is probably because macromolecular proteins have cavities into which a peptide can insert, thereby shielding many of the interactions from competition by solvent water. This kind of shielding is not possible for complexes between small peptides. Additionally, most peptides do not adopt stable secondary or tertiary structures, leading to the expectation that the entropic cost of forming a complex between small peptides would be much higher than binding of a peptide to a structurally well-defined protein. These very reasonable biases have presumably deterred efforts to identify such complexes and to use them in biotechnology applications. This bias was also supported by early efforts of the inventor and his co-workers to accomplish this goal through the use of well-established methods, including the yeast two-hybrid system (Fields and Song, 1989; Yang et al., 1995) and phage display (Burton, 1995). These approaches failed completely.

Figure 1B:
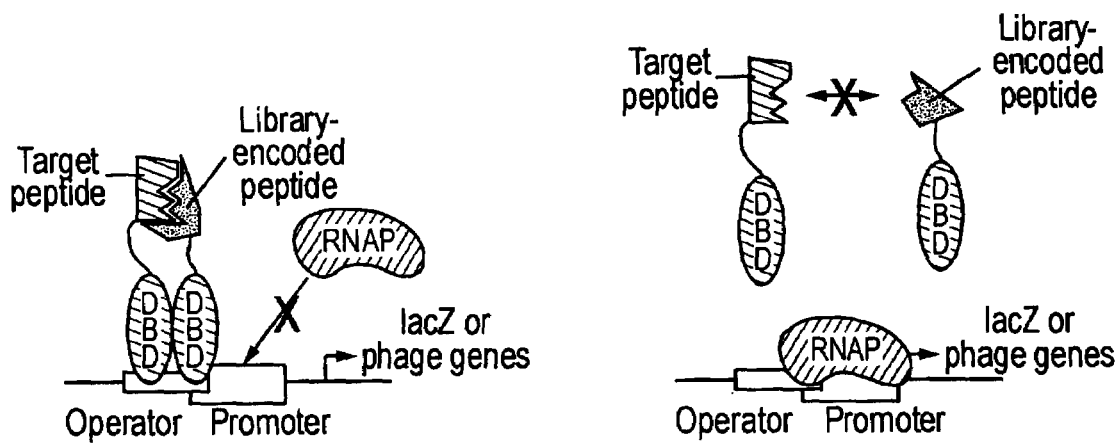

However, the inventor has now demonstrated that it is indeed feasible to isolate highly specific complexes between relatively small peptides. A simple genetic selection scheme (see FIGS. 1A–1B) is described that allows one to search a peptide library in living cells for molecules that bind a given target peptide with high specificity and reasonable affinity. In one case, a 13-residue sequence from the protease cleavage site of the human insulin-like growth factor-I (IGF-I) was employed as the target. A crude extract made from $E.$ $coli$ cells expressing either GST or the GST-target peptide fusion protein was applied to amylose columns saturated with either MBP, MBP-LEP27 or MBP-60a.a. (a fusion containing a 60 residue peptide unrelated to LEP27). After thorough washing, the bound proteins were eluted with maltose and analyzed by SDS-PAGE and staining with Coomassie Brilliant Blue. The GST-target peptide fusion was retained only by the MBP-LEP27 protein. No other proteins were observed. MBP-LEP27 did not retain GST alone from an extract. The 27-residue peptide which binds the 13-mer target with a $K_D$ of approximately $2\times10^{-5}$ M and very high specificity (as determined by affinity chromatography, see FIG. 2) was identified from a library of approximately 50,000 molecules. Using a larger library, a 15 mer (LEPB) that binds a 14 mer epitope that is part of human pro-IL-1β, using the same system (Zhang et al., 2000). This selection scheme is applicable to the identification of peptide ligands for almost any given target peptide.

Figure 2:
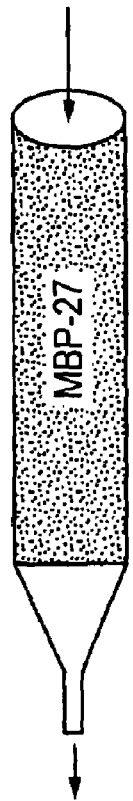
FIG. 2—Affinity purification of a recombinant protein based on peptide-peptide complexes isolated from the genetic assay. Scheme for purification of GST-13-mer (SEQ ID NO:5) by affinity chromatography using immobilized MBP-LEP27 (SEQ ID NO:6) (Zhang et al., 2000).
Figure 3:
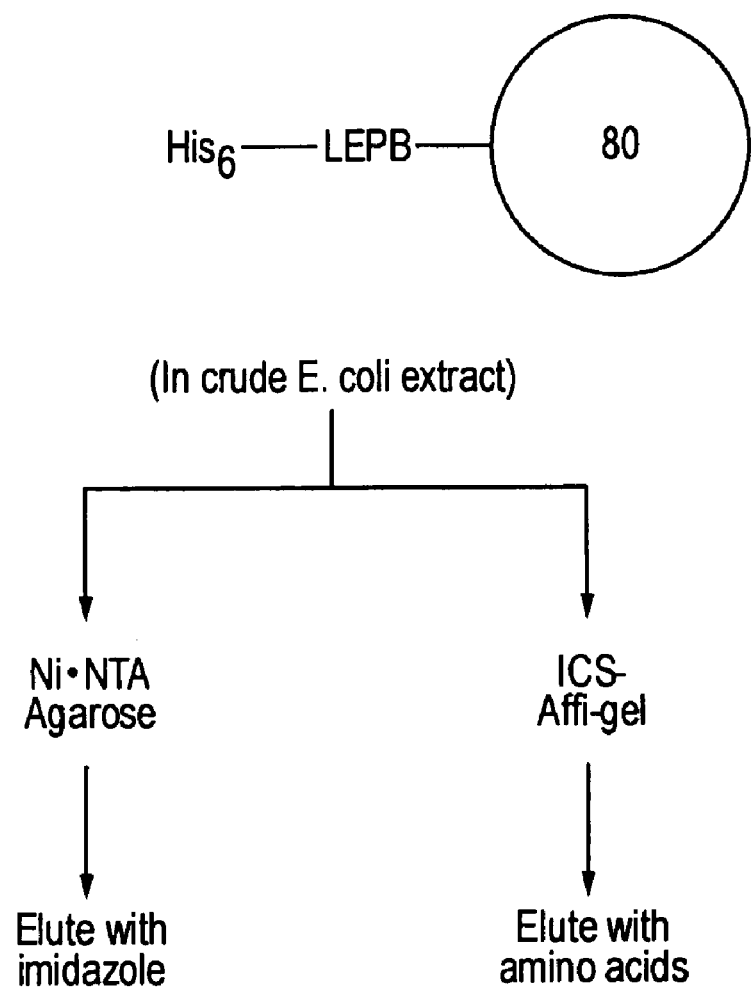
FIG. 3—Scheme for purification of a recombinant protein based on a peptide-peptide interaction. The yeast Gal80 protein was fused to two tags, six histidine and LEPB (a 15-mer selected to bind a 14-mer called ICS using the system shown in FIGS. 1A–B). This protein was expressed in E. coli. A crude extract was split and applied either to a standard Ni-NTA agarose resin (Qiagen) or to synthetic ICS peptide immobilized covalently on Affi-gel. The ICS peptide column provided a high level of purity of the LEPB-tagged protein.

The lambda Repressor reconstitution system has many advantages over other possible systems for selecting peptide-binding peptides. It is sensitive to even low affinity interactions, as is believed will be typical of peptide-peptide contacts. It is carried out in $E.$ $coli$, rather than slower-growing and less easily transformable yeast or higher cells. Finally, the fact that the assay is carried out in the presence of a large excess of other proteins (the cellular constituents of $E.$ $coli$), it is anticipated that the binding will be highly specific. This expectation has been borne out by affinity chromatography experiments (FIGS. 2 and 3).

An alternative transcriptional readout system for use according to the present invention is described by Dove et al. (1998), incorporated by reference herein.

B. Binding Partner Read-Out Systems

1. Lambda Repressor System

To search a peptide library for molecules that act as selective receptors for a given target peptide, an adaptation of a selection scheme developed by Hu et al. for the genetic analysis of leucine zipper interactions (Hu et al., 1990; Hu, 1995) was employed. Binding of λ Repressor dimers to cognate operator sites is reduced dramatically when the C-terminal dimerization domain is deleted. However, high affinity repressor-operator binding can be reconstituted by fusion of the DNA-binding domain (DBD) to a number of heterologous proteins or protein fragments that self-associate and functionally replace the native dimerization domain (Cairns et al., 1997; Jappelli and Brenner, 1996; Park and Raines, 2000). To adapt this assay for our purposes, two compatible constructs were made and transformed into $E.$ $coli$. One encoded the DBD fused to a target peptide (an epitope of 8–15 amino acids). The other expressed a fusion of the DBD with a library of DNA fragments fused to the DBD. Association of the library-encoded peptide (LEP) with the target peptide should reconstitute high-affinity repressor-operator binding. $E.$ $coli$ cells carrying a functional repressor are resistant to phage lambda infection, since the λ Repressor blocks the high-level transcription of genes essential for lytic growth (Ptashne, 1987). This protocol results in the isolation of many phage-resistant colonies, which include cells containing the desired peptide-binding peptides as well as false positives.

2. Elimination of False-Positives

Figure 4:
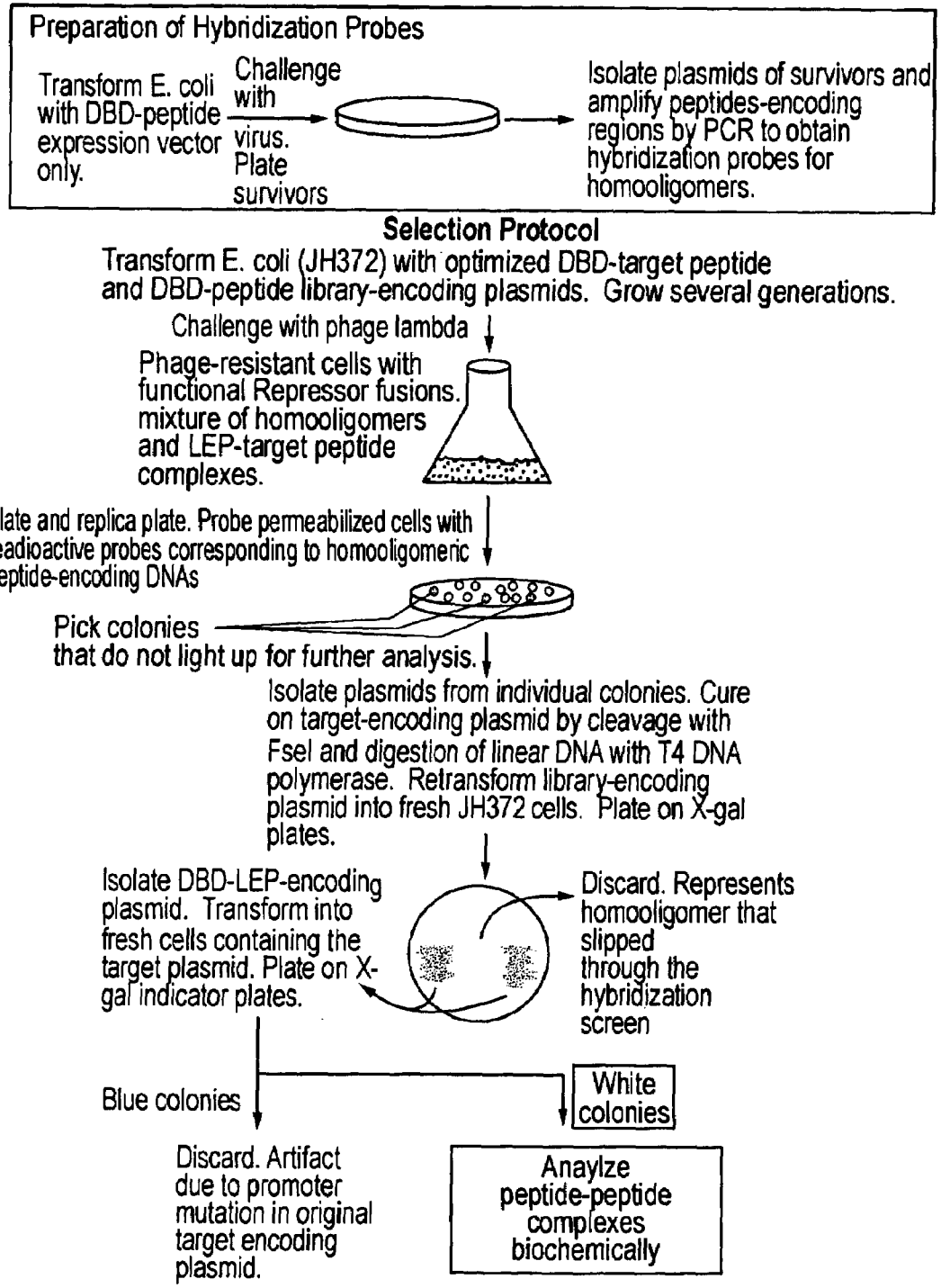
FIG. 4—Schematic representation of the protocol employed to eliminate most false positive in the Repressor reconstitution assay using biological methods.

"False positives," i.e., phage-resistant cells that nonetheless do not harbor an epitope-binding LEP, can result from several different events. The most common is direct or indirect LEP homooligomerization. Another is a promoter mutation that results in overexpression of the DBD-LEP fusion protein (the DBD alone retains a very weak dimerization capacity and will repress if expressed at very high levels). The protocol in FIG. 4 is designed to eliminate as many false positives as possible at the microbiology/molecular biology level, before proceeding to more labor-intensive biochemical analysis of the isolated peptide-peptide complexes. A two step process will be employed to eliminate the very common homooligomeric LEPs.

First, colony hybridization will be employed using DNA probes that correspond to the sequences encoding homooligomeric peptides. These probes will be obtained as follows. The entire library will be transformed into $E.$ $coli$ and challenged with phage in the absence of a target plasmid, thus selecting for homooligomeric peptides (the inventor has demonstrated the feasibility of this approach previously (Zhang et al., 1999)). All of the surviving colonies will be scraped off the plate and a preparation of total plasmid DNA will be carried out. This mixture will then be used as templates for a PCR™ amplification of the peptide-encoding regions. The primers will be complementary to conserved regions of the plasmid flanking the library-encoding regions. When a real selection for epitope-binding peptides is carried out, the survivors will be replica plated, and the new plate will be probed with these PCR™ products (radiolabeled with $^{32}$P). Very high stringency conditions will be employed such that annealing of the conserved region present in the PCR™ primers and the library-encoding plasmids will not lead to a positive signal. Only those cells that do not "light up" with the homooligomer probes will be processed further.

As a second step to ensure that repression is dependent on the presence of the DBD-target peptide expression plasmid, the inventor will cure the cells of the target-encoding plasmid and verify that efficient repression no longer occurs. Initially, the inventor did this by gel separation of the linearized library- and target-encoding plasmids, followed by religation of the library-encoding plasmid and transformation into fresh cells, but this is tedious. The inventor has placed a unique FseI site (recognition sequence 5'-GGCCG-GCC-3') (SEQ ID NO:7) in the target plasmid, allowing it to selectively linearize the target plasmid in a mixed preparation that also contains the library-encoding plasmid. The DNA preparation will then be treated with T4 DNA polymerase in the absence of dNTPs to allow the voracious exonuclease activity of this enzyme to degrade the linearized target-encoding DNA. The resultant DNA will be retransformed into fresh cells and the transformants will be streaked onto X-gal plates (the receptor strain employed in this assay, JH372, has an integrated lacZ gene under the control of a lambda operator (Hu et al., 1990)). The vast majority of cells will now contain only the library-encoding plasmid, so any survivors that make white patches at this point will be discarded. Of course, this protocol will result in the loss of a true positive if the library DNA contains FseI site. But this will occur very infrequently since it is an eight base pair site and is comprised entirely of C's and G's.

This two-step hybridization/target plasmid curing protocol should eliminate false positives due to the presence of homooligomeric library-encoded peptides completely and has the added advantage of also identifying false positives that result from overexpression of the DBD-LEP fusion protein.

To eliminate false positives due to promoter mutations in the target-encoding plasmid that result in overexpression, the DBD-LEP-encoding plasmids from the remaining apparent positives from the FIG. 4 protocol will be retransformed into fresh cells harboring the wild-type target plasmid. All of the transformants should be white when plated onto X-gal plates. If the cells are blue, they will be discarded. Finally, it is important to note that screens that require retransformation into fresh cells that have never seen virus will also eliminate false positives due to completely plasmid-independent events such as surface receptor mutations that block phage DNA uptake. With this optimized protocol, the inventor anticipates that it will take about a week to identify LEPs that bind any given target epitope and, of course, several different selections can be carried out simultaneously.

3. Biochemical Verification of LEP-epitope Binding.

Figure 5:
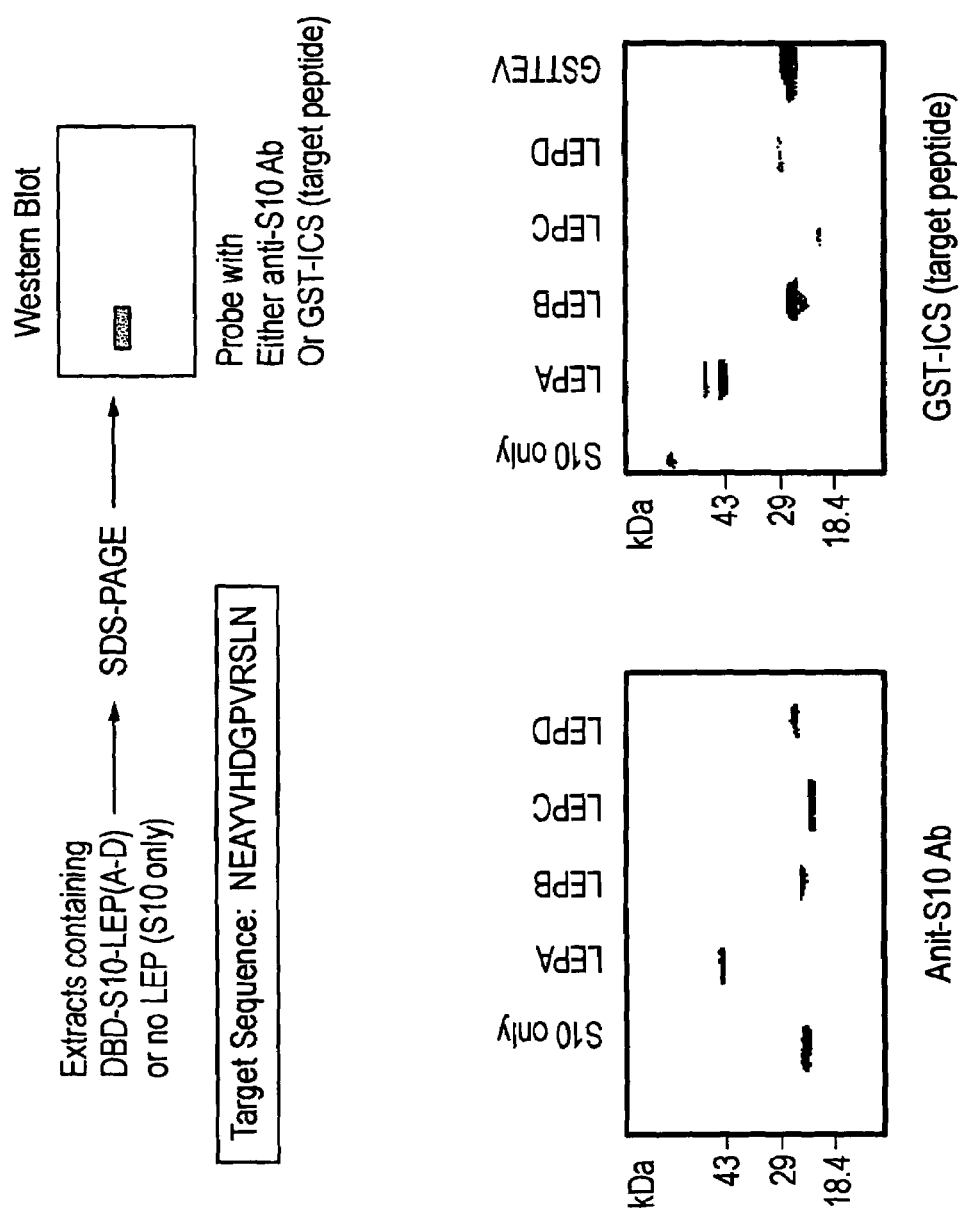
FIG. 5—"Far Western" blot protocol to eliminate false positives. An extract is prepared from phage-resistant cells that express the DBD-LEP fusion. This is electrophoresed through a denaturing gel, then blotted onto a membrane. This is probed with a GST fusion protein containing the target epitope, followed by labeled anti-GST antibody to visualize the site(s) of binding of the GST-peptide fusion protein. In this case, two of the four selected peptides provided strong signals, showing that they are true hits, while two (LEPC and LEPD, provided weak or unobservable signals, indicating that they are false positives, or binding peptides that associate too weakly to be of practical utility. LEPA=Large (40 kD) polypeptide; LEPB=KARKEAELAAATAEQ (SEQ ID NO:1); LEPC=PCP; LEPD=PCHLNCSLQTLSPTRTTPRKHCKHCFKTLSE KMKWN (SEQ ID NO:2).

The putative epitope-binding LEPs that survive the tests described above are then tested biochemically for epitope binding. In addition to verifying a biochemical interaction, it is important to distinguish very weak interactions from stronger ones that will prove of practical utility. This is done by expressing a GST fusion protein containing the target peptide at the C-terminus. This protein is then employed as a probe in a Far-Western blot experiment (FIG. 5). Crude extracts from cells that express the Repressor DBD-LEP fusion are electrophoresed through a denaturing gel and blotted onto a suitable surface, such a nitrocellulose. The blot is then probed with the GST-epitope fusion protein, followed by anti-GST antibody and finally an HRP-conjugated secondary to visualize the binding events. Lanes in which the band corresponding to the Repressor DBD-LEP is bound by the GST-epitope fusion protein are considered true hits.

Another method of utility is affinity chromatography. In this case, the target peptide is coupled to a chromatography resin, either as a synthetic peptide or as part of a fusion protein. An extract containing the LEP, fused to the Repressor DBD or some other protein, is then passed over the column. The extent of binding of the LEP-containing protein to the resin is then deduced by some convenient method such as SDS-PAGE after elution of all bound proteins from the column (see FIGS. 2 and 3). Peptides capable of binding selectively to the target epitope in this format are considered true positives and excellent candidates for further development as affinity chromatography agents.

Finally, the most rigorous tests for peptide-peptide interaction involve spectroscopic assays. These experiments provide quantitative data regarding the affinity of the LEP for the epitope target. For example, fluorescence polarization (Heyduk et al., 1996) can be employed. In this experiment, one of the peptides is synthesized with a covalently coupled fluorescein molecule. A low concentration of this species (usually $10^{-8}$ M to $10^{-10}$ M) is titrated with increasing amounts of a fusion protein containing the partner peptide. The increase in the polarization of the fluorescence as a result of binding of the low molecular weight fluorescein-peptide conjugate to the high molecular weight fusion protein is monitored.

4. List of Suitable Targets

An advantage of this technology is that it potentially allows the isolation of a peptide capable of binding almost any epitope. However, we are interested, in particular in protein epitopes that contain the sites of post-translational modifications that regulate the activity of the protein. This is because the EBM could potentially be employed as a reagent to control these events (see below for proof of principle). Some particularly important targets would be: (1) the epitopes contained within pro-interleukins that are cleaved by the corresponding maturases to provide the biologically active interleukin; (2) epitopes in transcription factors, such a Ik-B, NF-AT and SREBP that include residues that are either cut or phosphorylated to active their transcription potential, (3) epitopes in the extracellular oligomerization domains of E-cadherins (there is some evidence that molecules able to bind these sequences could promote movement of drugs across the blood-brain barrier); and (4) epitopes at the far N- or C-termini of any protein, which are expected to be available sites of EBMs to be employed as affinity chromatography agents.

C. Generation of Vectors

1. Design of Peptide Targets

Generally, there are few, if any, constraints on the design of potential peptide targets. Perhaps the only considerations are the generally considered minimum epitope size for a peptide—about 5–6 residues—and the statistical uniqueness in the human genome of about 8 residues.

2. Oligonucleotide Synthesis

Oligonucleotide synthesis is performed according to standard methods. See, for example, Itakura and Riggs (1980). Additionally, U.S. Pat. Nos. 4,704,362; 5,221,619, 5,583,013 each describe various methods of preparing synthetic structural genes.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

i) Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

ii) Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

iii) Polynucleotide Phosphorylase Method

This is an enzymatic method of DNA synthesis that can be used to synthesize many useful oligodeoxynucleotides (Gillam et al., 1978; Gillam et al., 1979). Under controlled conditions, polynucleotide phosphorylase adds predominantly a single nucleotide to a short oligodeoxynucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

iv) Solid-phase Methods

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic DNA synthesizers.

Phosphoramidite chemistry (Beaucage, and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

3. Library Synthesis

Peptide libraries are constructed at the DNA level by one of two methods. The first is to fragment genomic DNA, either by use of a four base cutter restriction enzyme, or by physical shearing, to provide a large number of small fragments that are then cloned downstream of the Repressor DNA-binding domain. The second is to encode a library of a specific length with synthetic oligonucleotides. This is standard practice in the field. A single-stranded oligonucleotide is synthesized with constant ends that include the appropriate restriction sites to allow subsequent cloning into the vector. The central part of the oligonucleotide is made random by programming the synthesizer to insert some mixture of all four natural nucleotides at each position. This can be adjusted to suppress stop codons if desired by restricting the identity of the third nucleotide in each codon. The resulting family of molecules is made double stranded by annealing a primer to the constant region on one end and replicating the rest of the molecule with a DNA polymerase. The ends are then cut with the appropriate restriction enzyme and the double-stranded DNAs are ligated into the "library vector." The entire collection of ligation products is then transformed into $E.$ $coli$, providing the library. This type of protocol is standard in the field and well known to experts in the area such as the inventor. Examples of this procedure can be found in the following references (Cwirla et al., 1990; Leuther et al., 1993; Needels et al., 1993).

4. Expression Constructs

The term "expression construct" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression constructs can contain a variety of "control sequences," which refer to nucleic acid sequences necessary for the transcription and possibly translation of an operably linked coding sequence in a particular host cell. In addition to control sequences that govern transcription and translation, vectors and expression constructs may contain nucleic acid sequences that serve other functions as well and are described infra.

i) Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline.

Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment.

ii) Other Regulatory Elements

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier & Sonenberg, 1988). IRES elements from two members of the picornavirus family (polio and encephalomyocarditis) have been described (Pelletier & Sonenberg, 1988), as well an IRES from a mammalian message (Macejak & Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997; herein incorporated by reference).

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3'-end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

iii) Vectors

The term "vector" is used to refer to a carrier nucleic acid molecule into which a nucleic acid sequence can be inserted for introduction into a cell. Typcially, the term vector also connotes the ability of the molecule to be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al. 1988 and Ausubel et al., 1994, both incorporated herein by reference).

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

iv) Cloning Techniques

Various standard cloning techniques will be utilized according to the present invention, including restriction, ligation, transformation, amplification, Southern and Northern blotting, etc. A comprehensive reference for these techniques is Sambrook et al. (1989).

v) Gene Transfer Techniques

Suitable methods for nucleic acid delivery for transformation of a cell for use with the current invention are believed to include virtually any method as would be known to one of ordinary skill in the art. Such methods include microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these cells may be stably or transiently transformed.

a. Direct Injection

In certain embodiments, a nucleic acid may be delivered to a cell via direct microinjection. Direct microinjection has been used to introduce nucleic acid constructs into Xenopus oocytes (Harland and Weintraub, 1985).

b. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

f. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

g. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

h. Microprojectile Bombardment

Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

D. Separation Technology

1. Chromatography

Any of a wide variety of chromatographic procedures may be employed according to the present invention. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In gas-liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material.

The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

2. Electrophoresis

Most electrophoresis embodiments will rely on polyacrylamide or agaraose media for separation.

i) Protein

Protein electrophoresis normally employs polyacrylamide resins, often using sodium dodecyl sulfate to facilitate size/charge separation. Other protein separations may be based on the isoelectric point of the protein. Protein gels also may be run under denaturing or non-denaturing conditions. Staining techniques such as Coomassie Stain and Silver Stain can be utilized on gel electrophoresed proteins.

ii) Nucleic Acids

Preparative and analytical nucleic acid electrophoresis may employ either agarose or polyacrylamide for a separation matrix, with the former preferred for larger fragments. Staining is usually accomplished with ethidium bromide. In other embodiments, nucleic acids may be integrally labeled with dyes or radiolabels.

E. Analytical Techniques

1. Western-blot & Far Western-blot

Western blots involve the use of antibodies to identify proteins that have been separated electophoretically. Typically, the electrophoresis is PAGE, either denaturing or non-denaturing depending on the target. Following separation, the gel is then "blotted" on to a suitable.

2. Mass Spectroscopy

While mass spectrometry-based characterization of multi-protein complexes is not a central focus of the invention, it is important to highlight at least one newly developed technique. Yates and coworkers (Link et al., 1999) have described a method for the identification of components of yeast multi-protein complexes that takes advantage of the fact that the sequence of the S. cerevisiae genome is known. A purified complex is denatured and subjected to a limit protease digest with trypsin or some other protease with a known sequence selectivity. The resultant complex mixture of peptides are then separated through two HPLC columns (a cation exchange followed by a reverse phase) linked sequentially and the eluate is introduced directly to a tandem mass spectrometer. These mass data are then transferred to a computer that is programmed with the masses of all possible yeast protein tryptic digestion products. The computer matches the experimental data to the data base and lists the proteins present in the original sample. More than 100 proteins can be uniquely identified in a single study using this completely hands-off technique.

Since the human genome sequence will soon be known, this extremely powerful technique can be applied to human biology problems in the near future. The sample requirements for this technique are about 1 μg of each individual protein detected. Thus, for a complex comprised of 20 proteins, a not insignificant quantity of about 20 μg must be purified. The main point is that, to employ DALPC or other powerful mass spectrometry-based identification tools, preparative quantities of the complex of interest must be purified, not a few nanograms as are suitable for Western blotting. This will be facilitated greatly if one had in hand an EBM capable of binding the native multi-protein complex. Thus, the full implementation of DALPC and related techniques will require the present invention to rapidly and easily purify interesting complexes on this scale.

3. NMR

Nuclear magnetic resonance (NMR) is occurs when the nuclei of certain atoms are immersed in a static magnetic field and exposed to a second oscillating magnetic field. Some nuclei experience this phenomenon, and others do not, dependening upon whether they possess a property called spin. Spin is effectively a small magnetic field, and can cause the nucleus to produce an NMR signal. NMR spectroscopy involves the use of NMR to study physical, chemical, and biological properties of matter, determining the structure more proteins and protein complexes. Time domain NMR spectroscopic techniques are used to probe molecular dynamics in solutions. Solid state NMR spectroscopy is used to determine the molecular structure of solids.

NMR samples generally are dissolved in a deuterium lock solvent, of which several are available. Most high resolution NMR samples are prepared and run in 5 mm glass NMR tubes. The animation window depicts a sample tube filled with solvent such that it fills the RF coil. The concentration of the sample should be great enough to give a good signal-to-noise ratio in your spectrum, yet minimize exchange effects found at high concentrations. The exact concentration will depend on the sensitivity of the spectrometer.

4. Quantification of Affinities & Measurement of Dissociation Constants

The affinities of the isolated peptides for their epitope targets can be determined by a number of methods. These include fusion of one or both of the interacting peptides to heterologous proteins, followed by the binding of one of the fusions to an affinity resin. The affinity of the partner fusion protein for this resin is then determined. Another common technique is surface plasmon resonance, in which one of the interacting peptides or fusion proteins is immobilized on an appropriately modified gold surface, and the on and off rates of the partner peptide are measured using the commercially available BIAcore instrument or an equivalent. The third method employed commonly by the inventor is fluorescence polarization, in which a fluorescently-labeled derivative of one of the peptides is titrated with the other (or the corresponding fusion protein) and the increase in the fluorescence polarization as a function of association is monitored.

There are many other techniques that could be employed to measure the affinity of the selected peptides for the epitope or a protein containing the epitope. These are generally well known to an expert in the field such as the inventor.

F. Methods to Improve Affinity of Low- to Moderate-Affinity Peptides

1. Co-oligomerization

One approach to improving the affinity of certain peptides is through co-oligomerization. For example, acryloyl-functionalized peptides can be co-oligomerized with acrylamide if they contain an acryloyl group, for example at their N-terminus (O'Brian-Simpson et al., 1997). To effect the synthesis of an N-acryloyl peptide, lysines on the LEPs would be protected with the MenPoc group (an o-nitrobenzyl-containing alcohol or amine protecting group) (Fodor et al., 1991; Jacobs and Fodor, 1994; McGall et al., 1997)or some other substituent that will survive the conditions used to deprotect Fmoc groups and cleave the synthetic peptide from the chain. After the reaction of the peptides and an activated ester derivative of acrylic acid, the lysines will be exposed by photochemical removal of the MenPoc group (UV irradiation at 350 nm. The peptide would then be co-polymerized with acrylamide by the addition of APS and TEMED. Conditions will be adjusted such that oligomers of about 50 residues are produced with approximately 10% of these being LEPs, with rest of polymer comprised of acrylamide, which will act as spacer. This will obviously be a mixed population of oligomers. The hope will be that at least some of the population will have the appropriate LEPs spaced at an appropriate distance to be able to bind in a chelating fashion the multi-protein complex of interest. This type of two-point binding is expected to lead to a substantial increase in the affinity of the LEPs for the complex relative to a single LEP-epitope interaction.

Two types of oligomers can be envisioned. One is where only a single LEP is included in the chain. These "homooligomers" would be anticipated to have an increased affinity from proteins containing the target epitope that exist as homodimers or higher order homooligomers. In the more general case, one can imagine co-polymerizing two different epitope-binding peptides that bind distinct epitopes in the same protein. These oligomers should be capable of tight two point binding to even monomeric proteins.

2. Cross-linking

Figure 6:
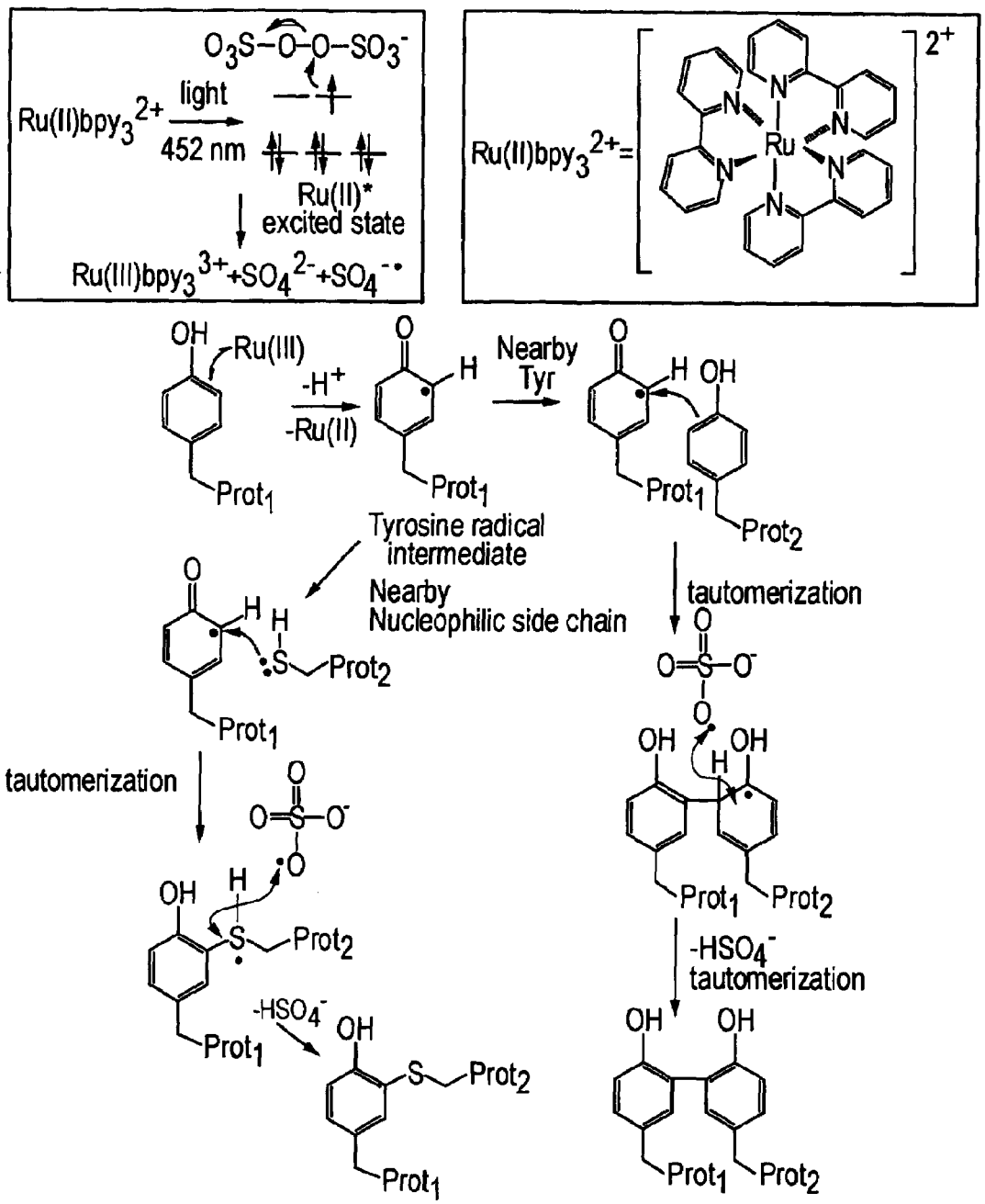
FIG. 6—Proposed mechanism of the photo-initiated protein cross-linking reaction using a ruthenium initiator.

The inventors are investigating a fundamentally different strategy to make the genetically selected peptides useful in various formats, including chip assays. As part of this project, the inventors have developed revolutionary new cross-linking chemistry that is a 1000-fold more efficient than known methods REFS. The reaction involves photolysis of metal complexes in the presence of an electron acceptor. This generates a high-valent metal complex that abstracts an electron from a protein tyrosine or tryptophan side chain. The resultant protein radical then couples rapidly with a nearby nucleophilic group (see FIG. 6). If that group is provided by a partner protein, an irreversible cross-link results. If the inventors were to include a tyrosine in the LEP (if it does not already contain one), it seems likely that the inventors could trap the non-covalent peptide-epitope complex covalently. The inventor has demonstrated that this reaction works well in crude extracts, so such a protocol could be carried out without the need for prior purification of the target protein. This should be particularly efficient when the epitope is in the context of the intact protein and the tyrosyl radical has a large surface on which it can couple. Since the peptide-epitope interaction is so specific, the inventor anticipates that this strategy can be employed to covalently couple an immobilized, genetically selected peptide to essentially only the target protein in a crude extract. If the peptide were labeled in some unique was, for example with biotin or a radiolabel, then the covalenlty trapped peptide-protein complex could be visualized easily or affinity purified.

3. Photo-trapping

A related strategy to improve affinity is to simply append the cross-linking reagent to the LEP rather than to employ it "in trans" as described above. This involves the chemical attachment of the appropriate metal-ligand complex to the peptide of interest. Particular examples would be derivatives of tris(2,2'-bipyridyl)Ru(II) dication (Fancy and Kodadek, 1999) or palladium(II) porphyrins (Kim et al., 1999). When activated photolytically or chemically, the appended cross-linkers would be expected to link the peptide to the target protein covalently. Experiments have demonstrated that molecules not closely associated are not cross-linked by these reagents, therefore covalent attachment of the peptide to the target protein is expected to be highly specific, reflecting the intrinsic binding properties of the peptide.

4. Mini-Pockets

It is the belief of the inventor that if one wishes to generate very high affinity epitope-binding molecules, it will be necessary to elaborate the simple epitope-binding peptides so as to form mini-pockets that will allow the epitope-receptor interactions to be better shielded from water. The inventor is exploring two such avenues of research, one which relies on organic chemistry-based approaches, and the other molecular biology. Each will involve a strategy not unlike the molecular forcep approach used by the CSH group, but with the critical difference that the arms of the forcep will be different. One will be the epitope-binding peptide (EBP) selected in the genetic assay, while the other will be either another peptide or a synthetic, non-peptide oligomer.

The chemical approach will involve the following steps. A library of oligomeric compounds (these could be peptides, peptoids or other non-peptidic species) will be synthesized by standard split/pool methods (Borman, 1997) on Tentagel beads. The library will then be capped with O-amino-α-hydroxyacetate to provide a site for specific attachment of an unprotected peptide segment. This will be accomplished by condensing the library with a peptide derivative produced by the oxidation of an N-terminal serine derivative of a genetically-selected peptide (Mikolajczyk et al., 1994; Rose et al., 1996). Resultant oxime formation will provide a library of "pincer" molecules, all of which contain two arms, one which is the genetically-selected peptide, the other of which is a library of oligomers. This bead-bound library will then be screened against the labeled epitope, or a protein containing the epitope, under conditions (determined empirically), where the genetically selected peptide dos not bind the epitope strongly enough to provide a hit. In other words, the inventor will ask for the "library arm" to participate in binding so as to provide a higher affinity interaction.

The chemistry described above for the construction of pincer libraries is favored, since the oxime connection between the library and the lead peptide is reversible (Rose et al., 1996), allowing recycling of the library. However, a number of other strategies could be conceived by an expert in the field of organic chemistry such as the inventor. In general, any chemistry that provides a reversible connection between the bead-bound library and the lead peptide is claimed.

Figure 7:
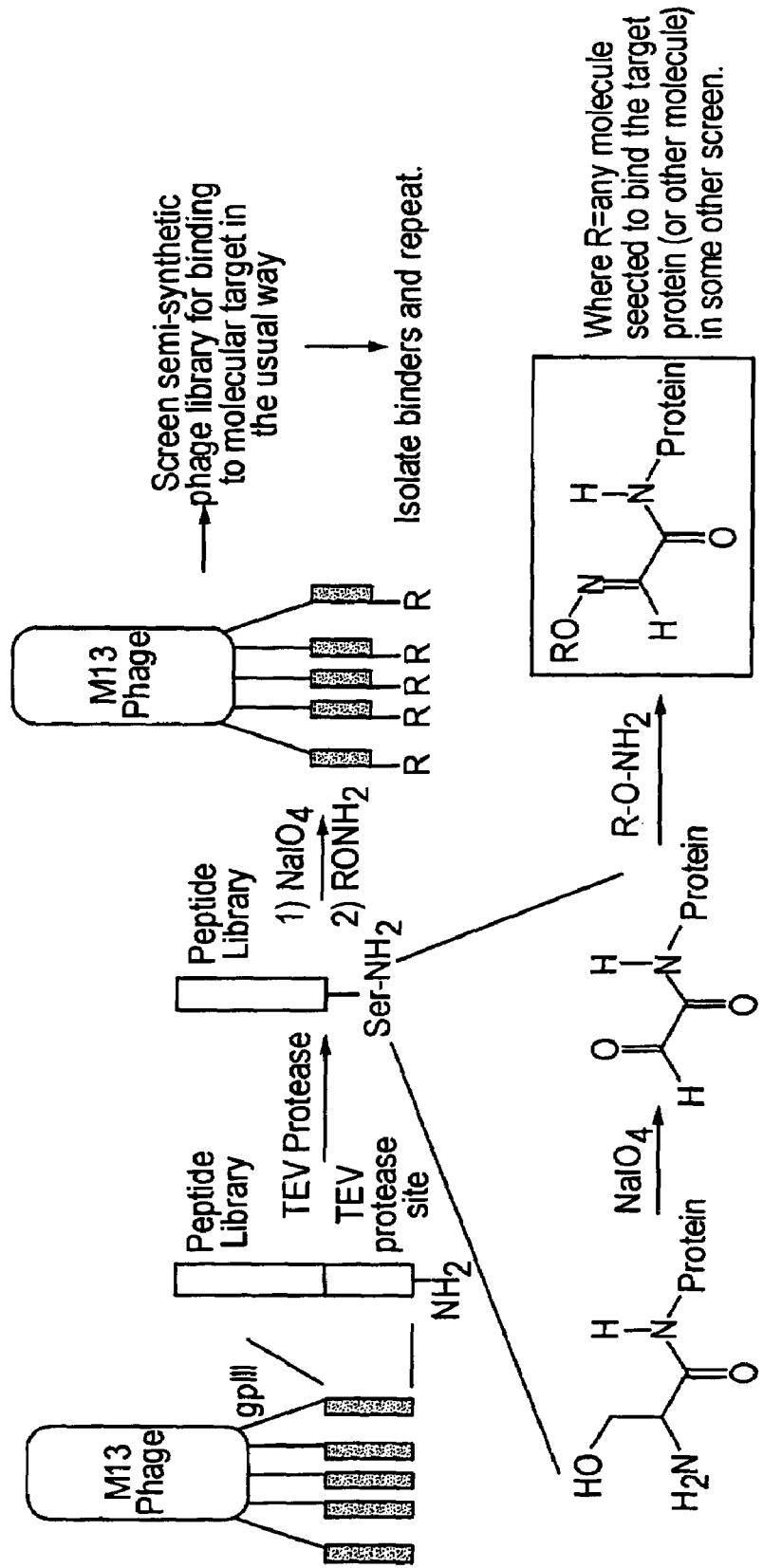
FIG. 7—Diagram of a "semi-synthetic phage display scheme in which a lead peptide is attached to a phage-displayed library. The resultant "pincer library, each of which contains the same lead peptide, can be screened for high affinity binders to a particular target protein.

The biological approach (see FIG. 7) will be similar in concept, except that the pincer library will be made and displayed on the surface of a bacteriophage. In this manifestation of the pincer concept, a phage displayed peptide library will be constructed using standard techniques with a specific protease site just N-terminal to it. This protease site will allow the exposure of an N-terminal serine after cleavage, which can, in turn, be oxidized selectively to an aldehyde. This provides a unique functional group on the surface of a phage to which an O-amino derivative of the genetically selected lead peptide can be attached via oxime formation (FIG. 7). Then, phage display will be employed to find phage that bind to an immobilized epitope target, again using conditions where the original peptide-epitope interaction is insufficient for stable association.

The inventor is confident that both of these approaches will provide high affinity epitope-binding molecules. Since all of the compounds in the library will have at least a µM affinity for the epitope, all that is required is for the library-derived molecules to add another three orders of magnitude to the overall affinity. Put another way, the inventor is looking for compounds that can wrap around the original peptide-epitope complex with a $K_D$ of at least $10^{-3}$ M, since coupled equilibria of $10^{-6}$ M and $10^{-3}$ M give an overall dissociation constant of $10^{-9}$ M, typical of a good monoclonal antibody-epitope complex.

Finally, it should be noted that both of the above schemes for the identification of pincer-type EBMs is novel and distinct from previous strategies by which molecules capable of two-point binding to a target have been obtained. Previously, all such molecules arose from the identification of two or more molecules capable of binding a target protein non-competitively (Hajduk et al., 1997; Maly et al., 2000; Shuker et al., 1996). A linker arm was then designed or discovered that allowed the two ligands to bind cooperatively. This is an effective, but tedious, process and thus is poorly suited for high-throughput applications. The method of the inventor, where the second arm of the pincer and the linker are selected in a single combinatorial screen is a significant advance over these methods.

G. Secondary Screens

1. Peptide Binding Studies

For screening the synthetic pincer libraries described above, relatively standard techniques will be employed. The epitope, or a protein containing it, will be labeled with an easily detectable molecule, such as fluorescein or biotin. This molecule will then be exposed to the library under demanding conditions (either low epitope concentration or high salt, etc.) so as to demand high affinity binding. Beads that bind the tagged protein, as visualized by fluorescence, for example, will be manually picked under a dissecting microscope. The identity of the variable oligomer will then be determined by direct sequencing using Edman degradation chemistry.

For screening the phage-displayed pincer libraries, a standard panning protocol will be employed, as described by the inventor previously (Han and Kodadek, 2000). An immobilized peptide comprising the epitope or an immobilized protein containing the epitope of interest will be employed as the target. Again, harsh conditions (determined empirically) will be employed that will require a very high affinity binding event. The identity of the phage-displayed peptide encoded by the library in the high affinity binders will be determined by DNA sequencing of DNA isolated from the phage.

2. Mutagenesis Procedures

In certain embodiments, it may be desirable to start with a given ligand and then attempt to alter its binding properties (affinity, specificity, stability, etc.). Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

i) Random Mutagenesis a. Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo(a)pyrene, N-acetoxy-2-acetyl aminofluorene and aflotoxin B1 cause GC to TA transversions in bacteria and mammalian cells. Benzo(a)pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo(a)pyrene-induced skin tumors contain A to T transformation in the second codon of the Ha-ras gene.

b. Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2–9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

c. In Vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

d. Random Mutagenesis by Fragmentation and Reassmbly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

ii) Site-Directed Mutagenesis

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as E. coli polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as E. coli cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multi-residue saturation mutagenesis are daunting (Warren et al., 1996, Brown et al., 1996; Zeng et al., 1996; Burton & Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

3. Chip Technology

Specifically contemplated by the inventor is the use of high affinity EBMs as capture agents in chip-based technologies. These techniques involve quantitative methods for analyzing large numbers of molecules rapidly and accurately. U.S. Pat. No. 5,143,854 describes large scale photolithographic solid phase synthesis of polypeptides and receptor binding screening thereof. U.S. Pat. Nos. 5,807,522 and 6,110,426 both provides methods for the fabrication of microarrays for biological samples. These technologies as well as related ones (Affymax) provide for the screening or large numbers of peptides or nucleic acids using automated and high throughput methods. Since the method discussed in this application will lead to the rapid discovery of large numbers of chemically synthesizable chemical ligands (as opposed to antibodies or other proteins that must be produced biologically), it is expected to fill an important need in the development of a commercial protein chip industry.

H. Substrate Directed Inhibition

Enzymes that covalently modify other proteins, such as proteases, kinases and phosphorylases, are very important pharmaceutical targets, since these modifications are often at the heart of signal transduction pathways that control many cellular processes. For example, the clinically used immunosuppressants cyclosporin A and FK-506 inhibit the phosphatase calcineurin in T-cells, blocking the dephosphorylation of transcription factor NF-AT, thereby inhibiting transcription of genes important in generating an immune response. Another example is the new class of anti-HIV drugs which bind to the HIV protease and prevent it from converting inactive viral polyproteins to their active, mature products. In fact, almost all known protease, kinase and phosphatase inhibitors target the enzyme itself, either directly and indirectly.

Figure 8:
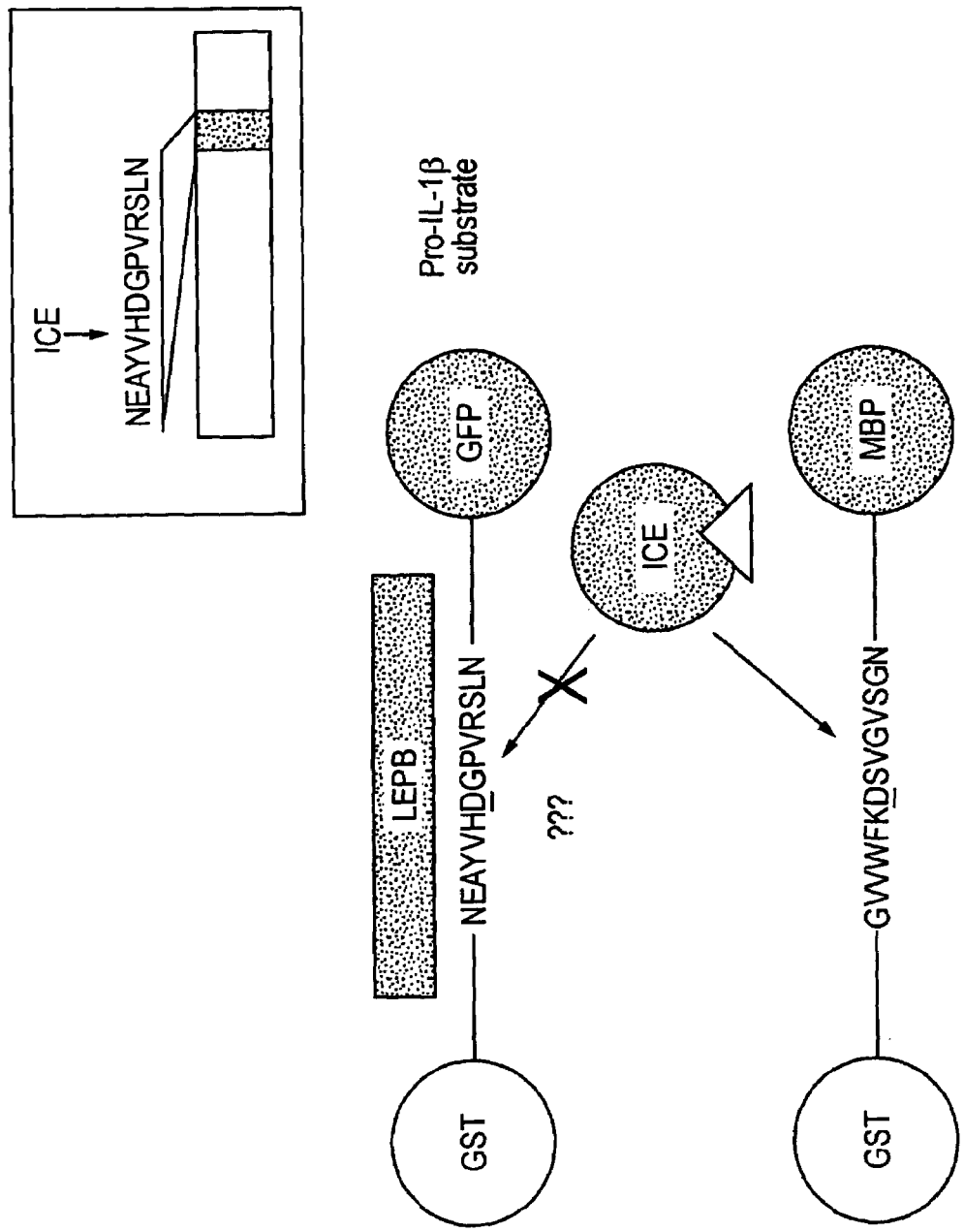
FIG. 8—Schematic diagram of a substrate-targeted protease inhibitor. This would be a novel application of EBMs capable of binding an epitope containing a protease cleavage site. Unlike common protease inhibitors, they could block processing of one, but not all, substrates of a particular enzyme. The same approach could theoretically be applied to the inhibition of phosphorylation events, ubiquitination and many other protein post-translational modifications (SEQ ID NO:3).

The inventor has developed a concept called substrate-directed inhibition (FIG. 8). The rationale is to discover compounds that bind to the segment of the substrate protein which is cut by the protease or phosphorylated or dephosphorylated by the kinase or phosphatase, respectively. Substrate-targeted inhibitors will have two very important advantages over traditional enzyme-targeted inhibitors. First, for enzymes that have a number of different substrates, one can block processing of a single substrate, but not others. Traditional inhibitors necessarily block all reactions catalyzed by the target enzyme. Since substrate-targeted inhibitors will be more specific, they may have fewer side effects if some activities of the enzyme are physiologically beneficial. Second, enzyme-targeted inhibitors often lose their potency over time due to mutations which allow the enzyme to escape binding to the inhibitor, but which have no effect on catalytic activity. A mutation which allowed the substrate to evade binding an inhibitor targeted to it would very likely also abolish enzyme-substrate recognition. Therefore, substrate-based inhibitors will probably have longer useful lifetimes, particularly in anti-bacterial and anti-viral applications, where genomic mutation can occur rapidly.

A general system to discover substrate-targeted inhibitors using the λ Repressor-based system is described. The peptide sequence recognized by the enzyme (i.e., the protease cleavage site, kinase phosphorylation site, etc.) is fused to the Repressor DNA-binding domain (DBD) and a peptide library fused to another copy of the Repressor DNA-binding domain is scanned for library-encoded peptides that bind the target peptide with high affinity and specificity (bottom of FIG. 1). The library-encoded peptides are then synthesized and evaluated as substrate-targeted inhibitors. These peptides may serve as lead compounds for the development of non-peptidic small molecule analogues, or may be used directly as drugs if tethered to a molecule that can deliver them into cells.

I. Examples

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The pro-IL-1β-derived epitope (ICS) was chosen for the reason that it includes one of the two sites cleaved by interleukin converting enzyme (ICE) during the hormone maturation process (Dinarello, 1998). If these cleavages do not occur, the hormone remains inactive. Since the inception of this project and well before Nestler's report of the inhibition of Ras farnesylation (Dong et al., 1999), we had hoped that epitope-binding molecules could be used as "protecting groups" for sites of post-translational modification in proteins such as proteolysis, phosphorylation, glycosylation, etc. What would be the advantage of such an approach over the use of traditional enzyme-targeted inhibitors? The vast majority of proteases, kinases, etc. have multiple cellular substrates. Of course, traditional enzyme-targeted inhibitors block the processing of all substrates acted upon by the enzyme. However, a substrate-targeted inhibitor holds out the possibility that processing of a single substrate could be blocked without affecting other reactions mediated by the same enzyme. Such a strategy might be advantageous if blocking one event mediated by a given enzyme had some therapeutic benefit, but blocking another resulted in toxicity. As a tool for basic research, such inhibitors could prove valuable in assessing the physiological consequences of various different post-translational modifications mediated by an enzyme with multiple substrates. Another scenario in which a substrate-targeted inhibitor might be useful is when the enzyme that mediates the post-translational modification event is unknown, making it difficult to develop classical inhibitors.

Figure 9:
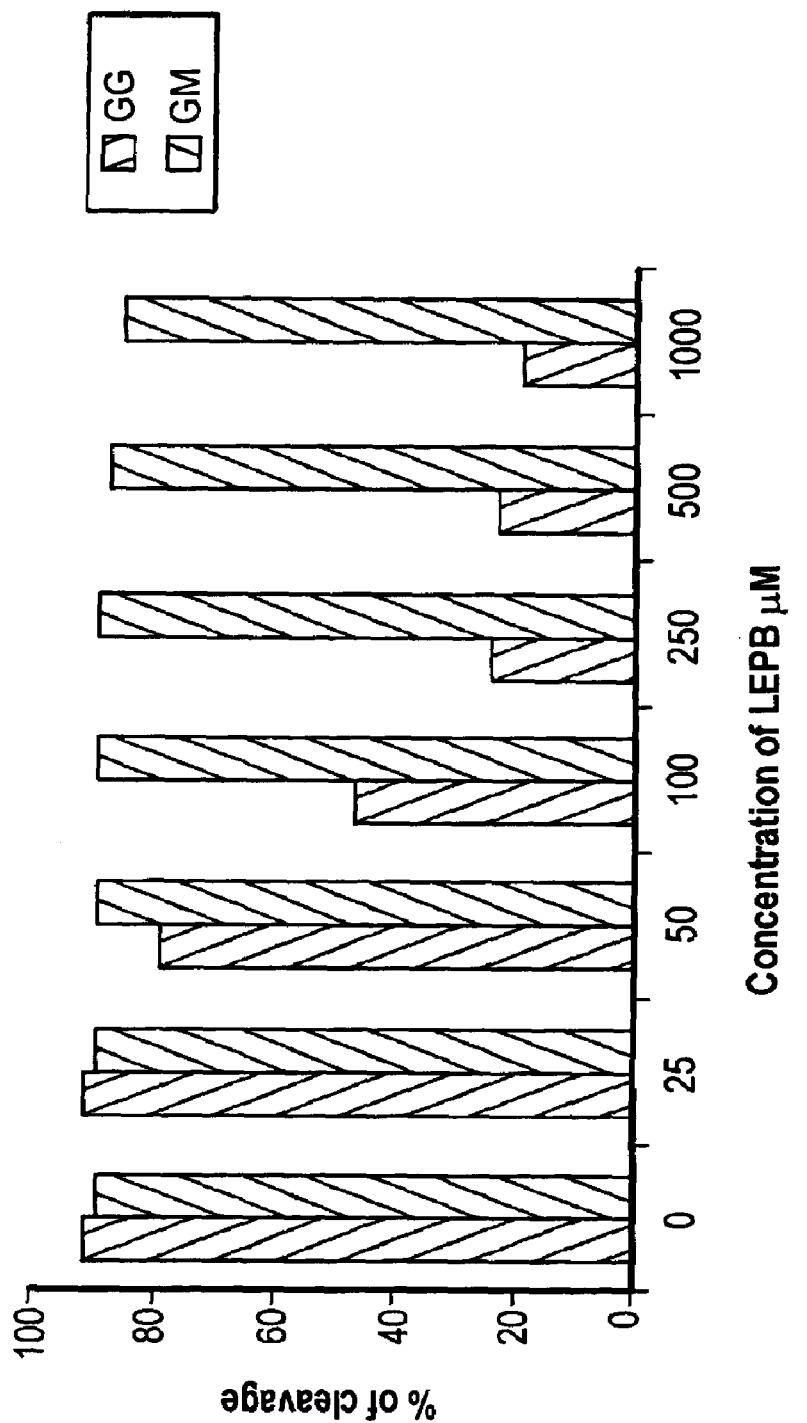
FIG. 9—Experimental demonstration of substrate-targeted inhibition of proteolysis using an epitope-binding peptide (LEPB). The experiment shown schematically in FIG. 5 was carried out. Addition of increasing amounts of LEPB to a reaction containing a protease and two different substrates inhibited one cleavage event, but not the other. Only the substrate containing the epitope recognized by LEPB was protected from cleavage. GG=GST$_{\text{NEAYVHDGPVRSLNGFP}}$ (SEQ ID NO:3); GM=GST$_{\text{GVVWFKDSVGVSGNMBP}}$ (SEQ ID NO:4); LEPB=KARKEAELAAATAEQ (SEQ ID NO:1).

Substrate-targeted inhibition could be achieved if the epitope-binding molecule recognized not only the residues required for the post-translational modification event, but also flanking residues unique to a given substrate. To test the feasibility of this idea, we constructed two different model substrates for ICE. Each was a fusion protein in which an N-terminal GST protein was linked to a C-terminal protein (GFP in "GG" and MBP in "GM", see FIG. 8). The linker in each case included a sequence known to be cleaved by ICE. In GG, the linker is the IL-1β-derived epitope against which LEPB was isolated. In GM, the proteins are linked by a sequence found in a different ICE substrate that shares little sequence homology with ICS other than the Asp in the cleavage site (see FIG. 8). Actually, this is a site in immature human ICE (activation is autocatalytic). Purified ICE cuts both the GG and GM substrates efficiently under these conditions. When synthetic LEPB was titrated into the reaction however, a progressive inhibition of the cleavage of GG, which contained the ICS epitope was observed (FIG. 9). The $IC_{50}$ was somewhere between 50–100 µM. However, LEPB addition had no detectable affect on GM cleavage. A control peptide taken at random from the library had no effect on either reaction (data not shown). It is noteworthy that the $IC_{50}$ measured in this experiment is well above the measured 2 µM $K_D$ of the LEPB-ICS complex. This probably reflects the fact that the peptide must compete with protease for the GG substrate. Alternatively, the $K_D$ was measured in a different context and while context is not qualitatively critical for binding, it probably modulates the association constant. In particular, this is the first experiment in which we have employed a peptide with a free N-terminus. It is conceivable the lack of any N-terminal extension could reduce binding.

This exciting result clearly demonstrates the feasibility of substrate-targeted inhibition of post-translational modification. This is, to the best of the inventor's knowledge, the first demonstration of a substrate-targeted protease inhibitor.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

J. References

The following references, to the extent that they provide exemplary procedural or other details supplementary to those set forth herein, are specifically incorporated herein by reference.

Ausubel et al., In: *Current Protocols in Molecular Biology*, John, Wiley and Sons, Inc., 1994.

Bates, "Genetic transformation of plants by protoplast electroporation," *Mol Biotechnol.*, 2(2):135–145, 1994.

Battraw and Hall, "Stable transformation of sorghum-bicolor protoplasts with chimeric neomycin phosphotransferase II and beta glucuronidase genes," *Theor. App. Genet.*, 82(2):161–168, 1991.

Bhattacharjee and Gupta, *J. Plant Bioch. and Biotech.* 6(2):69–73. 1997.

Boothman et al., *Cancer Res* 1989 Feb. 1;49(3):605–12

Borek, *Pharmacol Ther.* 1985;27(1):99–142

Borman, S. (1997). Combinatorial chemistry. Chem. & Eng. News 75, 43–62.

Bower et al., *The Plant Journal*, 2:409–416, 1992.

Braisted et al., *Proc Natl Acad Sci USA.* 1996 Jun. 11;93 (12):5688–92.

Burger, M. T., and Still, W. C. (1997). Simple strucutral requirements for sequence-selective peptide receptors? Tripeptide binding by a podand ionophore. J. Org. Chem. 62, 4785–4790.

Burks et al., *Proc Natl Acad Sci USA.* 1997 Jan. 21;94(2): 412–7.

Burton, D. R. (1995). Phage display. Immunotechnology 1, 87–94.

Cairns, M. T., Green, A. J., White, P. M., P. G., J., and Brenner, S. (1997). A novel bacterial vector system for monitoring protein-protein interactions in the cAMP-dependent protein kinase complex. Gene 185, 5–9.

Chandler et al., "RNA splicing specificity determined by the coordinated action of RNA recognition motifs in SR proteins," Proc Natl Acad Sci USA. 94(8):3596–3601, 1997.

Chen and Okayama, "High-efficiency transformation of mammalian cells by plasmid DNA," Mol. Cell. Biol. 7:2745–2752, 1987

Chen, C.-T., Wagner, H., and Still, W. C. (1998). Fluorescent, sequence-selective peptide detection by synthetic small molecules. Science 279, 851–853.

Cheng, Y., Suenaga, T., and Still, W. C. (1996). Sequence-selective peptide binding with peptido-A,B-trans-steroidal receptor selected from an encoded combinatorial receptor library. J. Amer. Chem. Soc. 118, 1813–1814.

Christou et al., Proc. Nat'l Acad. Sci. USA, 84(12):3962–3966, 1987.

Cwirla, S. E., Peters, E. A., Barrett, R. W., and Dower, W. J. (1990). Peptides on phage: A vast library of peptides for identifying ligands. Proc. Natl. Acad. Sci. USA 87, 6378–6382.

D'Halluin et al., "Transgenic maize plants by tissue electroporation," Plant Cell, 4(12):1495–1505, 1992.

Dinarello, C. A. (1998). Interleukin-beta, interleukin-18 and the interleukin-1 beta converting enzyme. Ann. N.Y. Acad. Sci. 856, 1–11.

Dong, D. L., Liu, R., Sherlock, R., Wigler, M. H., and Nestler, H. P. (1999). Molecular forceps from combinatorial libraries prevent the farnesylation of Ras by binding to its carboxyl terminus. Chem. & Biol. 6, 133–141.

Dove et al. (1998). Conversion of the w subunit of Eschericia coli RNA polymerase into a transcriptional activator or activation target. Gene and Development 12:745–754.

EP 0 273 085

Fairbrother, W. J., Christinger, H. W., Cochran, A. G., Fuh, G., Keenan, C. J., Quan, C., Shriver, S. K., Tom, J. Y. K., Wells, J. A., and Cunningham, B. C. (1998). Novel peptides selected to bind vascular endothelial growth factor target the receptor-binding site. Biochemistry 37, 17754–17764.

Fancy, D. A., and Kodadek, T. (1999). Chemistry for the analysis of protein-protein interactions: Rapid and efficient cross-linking triggered by long wavelength light. Proc. Natl. Acad. Sci. USA 96, 6020–6024.

Fechheimer et al., "Transfection of mammalian cells with plasmid DNA by scrape loading and sonication loading," Proc. Natl. Acad. Sci. USA 84:8463–8467, 1987

Fields, S., and Song, O.-k. (1989). A novel genetic system to detect protein-protein interactions. Nature 340, 245–246.

Fodor, S. P., Read, J. L., Pirrung, M. C., Stryer, L., Lu, A. T., and Solas, D. (1991). Light-directed, spatially addressable parallel chemical synthesis. Science 251, 767–773.

Fraley, Fomari, Kaplan, "Entrapment of a bacterial plasmid in phospholipid vesicles:potential for gene transfer," Proc Nat'l. Acad. Sci. USA 76:3348–3352, 1979.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Gillam et al., Gene. 1979 December; 8(1):81–97

Gillam et al., Gene. 1979 December; 8(1):81–97.

Gillam et al., J Biol Chem. 1978 Apr. 25;253(8):25

Gillam et al., J Biol Chem. 1978 Apr. 25;253(8):2532–9

Gopal, "Gene transfer method for transient gene expression, stable transformation, and cotransformation of suspension cell cultures," Mol. Cell. Biol. 5:1188–1190, 1985.

Graham and Van Der Eb, "A new technique for the assay of infectivity of human adenovirus 5 DNA," Virology 52:456–467, 1973

Griffiths, A. D., and Duncan, A. R. (1998). Strategies for selection of antibodies by phage. Curr. Opin. Biotechnol. 9, 102–108.

Hajduk, P. J., Sheppard, G., Nettesheim, D. G., Olejniczak, E. T., Shuker, S. B., Meadows, R. P., Steinman, D. H., Carrera, G. M., Marcotte, P. A., Walter, K., Smith, H., Gubbins, E., Simmer, R., Holzman, T. F., Morgan, D. W., Davidsen, S. K., Summer, J. B., and Fesik, S. W. (1997). Discovery of potent nonpeptide inhibitors of stromelysin using SAR by NMR. J. Amer. Chem. Soc. 119, 5818–5827.

Han, Y., and Kodadek, T. (2000). Peptides selected to bind the Gal80 repressor are potent transcriptoinal activation domains in yeast. J. Biol. Chem. 275, 14979–14984.

Harland and Weintraub, "Translation of mRNA injected into Xenopus oocytes is specifically inhibited by antisense RNA," J. Cell Biol. 101:1094–1099, 1985.

He et al., Plant Cell Reports, 14 (2–3):192–196, 1994.

Hensgens et al., "Transient and stable expression of gusA fusions with rice genes in rice, barley and perennial ryegrass," Plant Mol. Biol., 22(6):1101–1127, 1993.

Heyduk, T., Y., M., Tang, H., and Ebright, R. H. (1996). Fluorescence anisotropy: Rapid, quantitative assay for protein-DNA and protein-protein interactions. Method. Enzymol. 274, 492–503.

Hossain, M. A., and Schneider, H.-J. (1998). Sequence-selective evaluation of peptide side-chain interaction. New artificial receptors for selective recognition in water. J. Amer. Chem. Soc. 120, 11208–11209.

Hou and Lin, Plant Physiology, 111:166, 1996.

Hu, J. C. (1995). Repressor fusions as a tool to study protein-protein interactions. Structure 3, 431–433.

Hu, J., O'Shea, E. K., Kim, P. S., and Sauer, R. T. (1990). Sequence requirements for coiled-colis: Analysis with lambda Repressor-GCN4 leucine zipper fusions. Science 250, 1400–1403.

Inouye et al., "Up-promoter mutations in the lpp gene of Escherichia coli," Nucl. Acids Res., 13:3101–3109, 1985.

Itakura et al., J Am Chem Soc. 1975 Dec. 10;97(25):7327–32

Itakura et al., J Am Chem Soc. 1975 Dec. 10;97(25): 7327–32.

Jacobs, J. W., and Fodor, S. P. (1994). Combinatorial chemistry. Applications of light-directed chemical synthesis. Trends Biotechnol. 12, 19–26.

Jappelli, R., and Brenner, S. (1996). Interaction between cAMP-dependent protein kinase catalytic subunit and peptide inhibitors analyzed with λ Repressor fusions. J. Mol. Biol. 259, 575–578.

Kaeppler et al., Plant Cell Reports 9: 415–418, 1990.

Kaneda et al., "Introduction and expression of the human insulin gene in adult rat liver," J Biol Chem., 264(21): 12126–12129, 1989.

Kato et al., "Expression of hepatitis β virus surface antigen in adult rat liver," J. Biol. Chem., 266:3361–3364, 1991.

Khorana, Science. 1979 Feb. 16;203(4381):614–25

Khorana, Science. 1979 Feb. 16;203(4381);614–25.

Kim, K., Fancy, D. A., and Kodadek, T. (1999). Photoinduced protein cross-linking mediated by palladium porphyrins. J. Amer. Chem. Soc. 121, 11896–11897.

Knittel et al., *Plant Cell Reports*, 14(2–3):81–86, 1994.

Kodadek, T. (2001). Protein microarrays: prospects and problems. Chem. & Biol. 8, In press.

Lambert and Borek, *J Natl Cancer Inst.* 1988 Nov. 16;80 (18):1492–7

Landschulz, W. H., Johnson, P. F., and McKnight, S. L. (1990). The leucine zipper: A hypothetical structure common to a new class of DNA binding proteins. Science 240, 1759–1764.

Lazzeri, "Stable transformation of barley via direct DNA uptake. Electroporation- and PEG-mediated protoplast transformation," *Methods Mol. Biol.*, 49:95–106, 1995.

Lee et al., *Korean J. Genet.*, 11(2):65–72, 1989.

Leuther, K. K., Salmeron, J. M., and Johnston, S. A. (1993). Genetic evidence that an activation domain of GAL4 does not require acidity and may form a β sheet. Cell 72, 575–585.

Link, A. J., Eng, J., Schieltz, D. M., Carmack, E., Mize, G. J., morris, D. R., Garvik, B. M., and Yates, J. R. I. (1999). Direct analysis of protein complexes using mass spectrometry. Nature Biotechnol. 17, 676–682.

Macejak and Samow, "Internal initiation of translation mediated by the 5' leader of a cellular mRNA," *Nature*, 353:90–94, 1991.

Maly, D. J., Choong, I. C., and Ellman, J. A. (2000). Combinatorial target-guided ligand assembly: identification of potent subtype-selective c-Src inhibitors. Proc. Natl. Acad. Sci. USA 97, 2419–2424.

McCabe and Martinell, *Bio-Technology*, 11(5):596–598, 1993.

McGall, G. H., Barone, A. D., Diggelmann, M., Fodor, S. P. A., Gentalen, E., and Ngo, N. (1997). The efficiency of light-directed synthesis of DNA arrays on glass substrates. J. Amer. Chem. Soc. 119, 5081–5090.

Mikolajczyk, S. D., Meyer, D. L., Starling, J. J., Law, K. L., Rose, K., Dufour, B., and Offord, R. E. (1994). High yield, site-specific coupling of N-terminally modified beta-lactamase to a proteolytically-derived single-sulfhydryl murine Fab. Biooconj. Chem. 5, 636–646.

Needels, M. C., Jones, D. G., Tate, E. H., Heinkel, G. L., Kochersperger, L. M., Dower, W. J., Barrett, R. W., and Gallop, M. A. (1993). Generation and screening of an oligonucleotide-encoded synthetic peptide library. Proc. Natl. Acad. Sci. USA 90, 10700–10704.

Nicolau and Sene, "Liposome-mediated DNA transfer in eukaryotic cells: dependence of the transfer efficiency upon the type of liposomes used and the host cell cycle stage," *Biochem. Biophys. Acta,* 721:185–190, 1982.

Nicolau and Sene, "Liposome-mediated DNA transfer in eukaryotic cells: dependence of the transfer efficiency upon the type of liposomes used and the host cell cycle stage," *Biochem. Biophys. Acta,* 721:185–190, 1982.

Nicolau et al., "Liposomes as carriers for in vivo gene transfer and expression," *Methods Enzymol.,* 149:157–176, 1987.

O'Brian-Simpson, N. M., Ede, N. J., Brown, L. E., Swan, J., and Jackson, D. C. (1997). Polymerization of unprotected peptides: A view towards synthetic peptide vaccines. J. Amer. Chem. Soc. 119, 1183–1188.

Omirulleh et al., "Activity of a chimeric promoter with the doubled CaMV 35S enhancer element in protoplast-derived cells and transgenic plants in maize," *Plant Mol. Biol.,* 21:415–28, 1993.

O'Shea, E. K., Rutkowski, R., and Kim, P. S. (1992). Mechanism of specificity in the Fos-Jun oncoprotein heterodimer. Cell 68, 699–708.

Park, S.-H., and Raines, R. (2000). Genetic selection for dissociative inhibitors of designated protein-protein interactions. Nature Biotechnol. 18, 847–851.

PCT Application No. WO9217598

PCT Application No. WO94/09699

PCT Application No. WO95/06128

Pelletier and Sonenberg, "Internal initiation of translation of eukaryotic mRNA directed by a sequence derived from poliovirus RNA," *Nature,* 334:320–325, 1988.

Perales et al., "Gene transfer in vivo: sustained expression and regulation of genes introduced into the liver by receptor-targeted uptake," *Proc. Natl. Acad. Sci. USA,* 91:4086–4090, 1994.

Potrykus et al., *Mol. Gen. Genet.,* 199:183–188, 1985.

Potter et al., "Enhancer-dependent expression of human k immunoglobulin genes introduced into mouse pre-B lymphocytes by electroporation," *Proc Nat'l Acad. Sci. USA,* 81:7161–7165, 1984.

Rader, C., and Barbas, C. F. (1997). Phage display of combinatorial antibody libraries. Curr. Opin. Biotechnol. 8, 503–508.

Rhodes et al., "Transformation of maize by electroporation of embryos," *Methods Mol. Biol.,* 55:121–131, 1995.

Rippe, Brenner and Leffert, "DNA-mediated gene transfer into adult rat hepatocytes in primary culture," *Mol. Cell Biol.,* 10:689–695, 1990.

Rose, K., Zeng, W., Regamey, P.-O., Chernushevich, I. V., Standing, K. G., and Gaertner, H. F. (1996). Natural peptides as building blocks for the synthesis of large protein-like molecules with hydrazone and oxime linkages. Bioconj. Chem. 7, 552–556.

Schneider et al., *Angew Chem Int Ed Engl* 1999 Oct. 4;38(19):2894–2896

Schneider et al., *Angew Chem Int Ed Engl* 1999 Oct. 4;38(19):2894–2896.

Shao, Y., and Still, W. C. (1996). Sequence-selective receptors of peptides. A simple molecular design for construction of large combinatorial libraries of receptors. J. Org. Chem. 61, 6086–6087.

Shuker, S. B., Hajduk, P. J., Meadows, R. P., and Fesik, S. W. (1996). Discovering high-affinity ligands for proteins: SAR by NMR. Science 274, 1531–1534.

Singsit et al., "Expression of a *Bacillus thuringiensis* cryIA (c) gene in transgenic peanut plants and its efficacy against lesser cornstalk borer," *Transgenic Res.,* 6:169–76, 1997.

Still, W. C. (1996). Discovery of sequence-selective peptide binding by synthetic receptors using encoded combinatorial libraries. Acc. Chem. Res. 29, 155–163.

Torbet et al., "Transformation of oat using mature embryo-derived tissue cultures," *Crop Science,* 38:226–231, 1998.

Torbet et al., "Use of paromomycin as a selective agent for oat transformation," *Plant Cell Reports,* 14:635–640, 1995.

Tsukada et al., *Plant Cell Physiol.,* 30(4)599–604, 1989

Tur-Kaspa, Teicher, Levine, Skoultchi and Shafritz, "Use of electroporation to introduce biologically active foreign genes into primary rat hepatocytes," *Mol. Cell Biol.,* 6:716–718, 1986.

U.S. Pat. No. 4,659,774
U.S. Pat. No. 4,683,202
U.S. Pat. No. 4,684,611
U.S. Pat. No. 4,704,362
U.S. Pat. No. 4,816,571
U.S. Pat. No. 4,952,500
U.S. Pat. No. 4,959,463
U.S. Pat. No. 5,141,813

U.S. Pat. No. 5,143,854
U.S. Pat. No. 5,220,007
U.S. Pat. No. 5,221,619
U.S. Pat. No. 5,264,566
U.S. Pat. No. 5,284,760
U.S. Pat. No. 5,302,523
U.S. Pat. No. 5,322,783
U.S. Pat. No. 5,354,670
U.S. Pat. No. 5,366,878
U.S. Pat. No. 5,384,253
U.S. Pat. No. 5,389,514
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,583,013
U.S. Pat. No. 5,591,616
U.S. Pat. No. 5,602,244
U.S. Pat. No. 5,610,042
U.S. Pat. No. 5,635,377
U.S. Pat. No. 5,789,166
U.S. Pat. No. 5,789,215
U.S. Pat. No. 5,798,208
U.S. Pat. No. 5,807,522
U.S. Pat. No. 5,830,650
U.S. Pat. No. 5,925,565
U.S. Pat. No. 5,928,906
U.S. Pat. No. 5,935,819
U.S. Pat. No. 6,110,426

Van Eck et al., *Plant Cell Reports,* 14(5):299–304, 1995.
Wagner et al., *Proc. Natl. Acad. Sci.* 87(9):3410–3414, 1990.
Witte et al., *Cancer Res.* 1989 Sep. 15;49(18):5066–72
Wong et al., "Appearance of β-lactamase activity in animal cells upon liposome mediated gene transfer," *Gene,* 10:87–94, 1980.
Wu and Wu, "Receptor-mediated in vitro gene transfections by a soluble DNA carrier system," *J. Biol. Chem.,* 262: 4429–4432, 1987.
Wu and Wu, *Adv. Drug Delivery Rev.,* 12:159–167, 1993.
Wu and Wu, *Biochemistry,* 27:887–892, 1988.
Yang, Burkholder, Roberts, Martinell and McCabe, "In vivo and in vitro gene transfer to mammalian somatic cells by particle bombardment," *Proc Nat'l Acad Sci. USA,* 87:9568–9572, 1990.
Yang, M., Wu, Z., and Fields, S. (1995). Protein-peptide interactions analyzed with the two-hybrid system. Nucl. Acids Res. 23, 1152–1156.
Zhang, Z., Murphy, A., Hu, J. C., and Kodadek, T. (1999). Genetic selection of short peptides that support protein oligomerization in vivo. Current Biol. 9, 417–420.
Zhang, Z., Zhu, W., and Kodadek, T. (2000). Selection and practical applications of peptide-binding peptides. Nature Biotechnol. 18, 71–74.
Zhou, Broxmyer, Cooper, Harrington, and Srivastava "Adeno-associated virus 2 mediated gene transfer in murine hematopoietic cells, Exp. Hematol (N.Y.), 21:928–933, 1993.
Zhu, W., Williams, R. S., and Kodadek, T. (2000). A Cdc6-binding peptide selected using a bacterial two-hybrid-like system is a cell cycle inhibitor. J. Biol. Chem. 275, 32098–32105.

```
                              SEQUENCE LISTING

<160> NUMBER OF SEQ ID NOS: 15

<210> SEQ ID NO 1
<211> LENGTH: 3684
<212> TYPE: DNA
<213> ORGANISM: Artificial Sequence
<220> FEATURE:
<223> OTHER INFORMATION: Description of Artificial Sequence:cDNA copy of
      the nucleotide sequence of the genome of TNV-A

<400> SEQUENCE: 1
agtattcata ccaagaatac caaataggtg caaggcctta ctcagctaaa gagtctaaaa     60
tggagctacc aaaccaacac aagcaaacgg ccgccgaggg tttcgtatct ttcctaaact    120
ggctatgcaa cccatggaga cgacagcgaa cagtcaacgc tgcagttgcg ttccaaaaag    180
atcttctcgc cattgaggat tccgagcatt tggatgacat caatgagtgt ttcgaggagt    240
ctgctggggc acaatctcag cgaactaagg ttgtcgccga cggagcatat gcccccgcaa    300
aatccaacag gacccgccga gttcgtaagc agaagaagca caagtttgta aaatatcttg    360
tcaacgaagc tcgtgccgag tttggattgc ccaaaccaac tgaggcaaac agacttatgg    420
tccaacattt cttgctcaga gtgtgcaagg attggggcgt tgttactgcc cacgtacacg    480
gcaatgttgc actagctttg ccactggtgt tcatcccaac ggaagatgat ctgctatcac    540
gagcattgat gaacacacat gctactagag ccgctgtacg aggcatggac aatgtccaag    600
gggaggggtg gtggaacaat aggttgggga ttgggggcca ggtcggactg gccttccggt    660
```

```
ccaaataggg gtgccttgaa aggaggccag gattctccac gtccgtttcg cgtggggaac    720
atcctgatct ggtggtcata ccatcagggc gccctgagaa acagcgtcag ttgttacgct    780
atagtggtat aggcggccat ttattaatcg gcatccacaa caactctctt tccaacctgc    840
gtagggcttg atggaaaga gtattctatg tcgaggggcc caatgggctt caagacgccc    900
ctaagcccgt caaggagct tttcgaaccc ttgataagtt tcgtgatctc tatactaaaa    960
atagttggcg tcatacccct gtaactagtg aacaattcct aatgaattac acgggcagga   1020
aactgactat ttacagagag gcggttgata gtttgtcgca tcaaccccct agctcacgag   1080
atgcgaaact aaagacattc gtgaaggccg aaaaattaaa tctttctaag aagcctgacc   1140
ctgctcccag ggtcatccaa cctagatcgc ctcggtataa cgtttgtttg ggcaggtacc   1200
tccgacatta tgagcatcac gcgtttaaaa ccattgccaa gtgctttggg gaaatcacgg   1260
tcttcaaagg gtttactctg gagcaacaag gggaaatcat gcgctcgaag tggaataaat   1320
atgttaatcc cgtcgcagtc ggactcgacg ccagtcgttt cgaccaacac gtgtctgttg   1380
aagcactcga gtatgagcat gaattttacc tcagagacta cccaaatgat aaacagctaa   1440
aatggctgct aaagcagcaa ttgtgcaacg taggaacggc attcgccagt gacggcatta   1500
taaaatacaa gaagaagggt tgtagaatga gcggagacat gaacacgagt ttgggcaact   1560
gcattctaat gtgcgccatg gtctacgggt tgaaagaaca cttaaacatc aatttgtccc   1620
ttgcaaataa tggggatgac tgcgtcattg tctgtgagaa agcggattta agaaattga   1680 caagcagcat cgagccatat ttcaagcagt ttggattcaa gatggaagtg gaaaaacccg   1740
tggatatatt tgagcgcata gaattttgcc aaacccaacc tgtgttcgat ggatcccagt   1800
acatcatggt acgcaaacct tctgtggtaa catctaaaga cgtcactagc cttatcccat   1860
gtcaaacgaa agcacaatac gcagaatggc tgcaagctgt aggtgagtgt ggcatgagca   1920
ttaacggtgg gattcctgtc atgcagaatt ctaccaaaaa gctccaaact ggcatccgcc   1980
gcacaaaatt caccaagacc ggcgagttcc agacgaacgg attggggtat cactctagat   2040
atatgcatag agtggcccgg gttccttcgc ctgaaacccg tttatccttc tatctagctt   2100
tcggtatcac accagacctc caagaagcat tggagatctt ctatgatacc cacaggcttg   2160
agttggatga tgttatccca actgataacct accaagtgtc aggagagcat ttgatcaatg   2220
gattaccaaa ctgatgtaac ggaggacaat gtgcaaatac gcggtcgggc taggagcgtt   2280
gagggtaaga aacacaatgg ttcgggatta actggcgtta agcgtcacgc ggtgagcgaa   2340
acatctcaga aatcacagca aggtactggc aatggaacta tgaccaatat agccgaagaa   2400
cagaccatta ccgtgacata caactttaac ttttaagtta tggctgcgtg tcgctgttgt   2460
gatacttcac caggtattac actattccct tactttgcaa ttctcatcct tatattggca   2520
atacttgttg tagggactcc caatcaacaa tatcaccatt ctccaagcac ttacgagtac   2580
aagactcaac acatttcgat cgcaaaatag acatggcagg aaagaagaac aacaacaacg   2640
gtcagtatat aatactgcgt actccagagc aacaggtgga gatagaccag cgcaacgccc   2700
gtcgtgctca aatgggtcgc atgaagaagg ctagacagcc cgttcagcga tacttacagc   2760
aacacgggtt gcgaaacgga ttgtccggta gagggggcta catagtggct cccacctccg   2820 gggggttgt cactcgaccc atagtgccga aattctccaa caggggagat tccactatag   2880
tccgtaacac tgagattttg aacaaccaaa tcttagcggc gctaggcgca ttcaatacaa   2940
caaactccgc actgattgca gcagcaccat catggctggc tagcatcgct gatctttaca   3000
gtaaatacag atggctctca tgtgagatca tctacattcc aaaatgcccc accaccacca   3060
```

```
gtggatcaat tgccatggct ttcacatacg acagaaatga cgctgcaccc accgcaaggg    3120
ctcagctgtc acaatcttac aaggccatca attttccacc gtatgcggga tacgacggag    3180
cagcatattt gaattcgaac cagggagctg ggtcagccat cgccgttcaa cttgatgtta    3240
ccaagttgga caagccatgg tacccccacta tctcctctgc cggcttcggg gcgctcagcg    3300
tcctcgatca gaaccaattc tgcccgcgt cccttgtggt cgctagcgat ggggacccg      3360 ctactgctac tccagcaggg gaccttttca tcaagtacgt gattgagttc attgaaccaa    3420
tcaacccaac aatgaacgtc tagttctttg tactgtaact tggctaatgc ctaaggtgga    3480
gtcacaccat tggagacgga gacggatcct gggaaacagg cttgacgggc gggggtggt    3540 gcccccgacg acgcatcact ccggatacca atggtacacc actatggcag ggtctgccaa    3600
ggtcttgtgc accaagaacc cctggaaacg gggggaggg gggtagcaca tatcatccag     3660
attgaggggc ctttgcccca cccc                                            3684

<210> SEQ ID NO 2
<211> LENGTH: 6395
<212> TYPE: DNA
<213> ORGANISM: Artificial Sequence
<220> FEATURE:
<223> OTHER INFORMATION: Description of Artificial Sequence: cDNA copy
      of the nucleotide sequence of the genome of TMV-U1

<400> SEQUENCE: 2
gtatttttac aacaattacc aacaacaaca acaacaaac aacattacaa ttactattta      60
caattacaat ggcatacaca cagacagcta ccacatcagc tttgctggac actgtccgag    120
gaaacaactc cttggtcaat gatctagcaa agcgtcgtct ttacgacaca gcggttgaag    180
agtttaacgc tcgtgaccgc aggcccaagg tgaactttc aaaagtaata agcgaggagc      240
agacgcttat tgctacccgg gcgtatccag aattccaaat tacattttat aacacgcaaa     300
atgccgtgca ttcgcttgca ggtggattgc gatctttaga actggaatat ctgatgatgc     360
aaattcccta cggatcattg acttatgaca taggcgggaa ttttgcatcg catctgttca     420
agggacgagc atatgtacac tgctgcatgc ccaacctgga cgttcgagac atcatgcggc     480
acgaaggcca gaaagacagt attgaactat acctttctag gctagagaga gggggaaaa     540 cagtccccaa cttccaaaag gaagcatttg acagatacg agaaattcct gaagacgctg      600
tctgtcacaa tactttccag acaatgcgac atcagccgat gcagcaatca ggcagagtgt     660
atgccattgc gctacacagc atatatgaca taccagccga tgagttcggg gcggcactct     720
tgaggaaaaa tgtccatacg tgctatgccg ctttccactt ctctgagaac ctgcttcttg     780
aagattcata cgtcaattttg gacgaaatca acgcgtgttt ttcgcgcgat ggagacaagt    840
tgaccttttc ttttgcatca gagagtactc ttaattattg tcatagttat tctaatattc     900
ttaagtatgt gtgcaaaact tacttcccgg cctctaatag agagggttac atgaaggagt     960
ttttagtcac cagagttaat acctggtttt gtaagttttc tagaatagat acttttctt     1020 tgtacaaagg tgtggcccat aaaagtgtag atagtgagca gttttatact gcaatggaag    1080
acgcatggca ttacaaaaag actcttgcaa tgtgcaacag cgagagaatc ctccttgagg    1140
attcatcatc agtcaattac tggttttccaa aatgagggga tatggtcatc gtaccattat    1200
tcgacatttc ttttggagact agtaagagga cgcgcaagga agtcttagtg tccaaggatt    1260
tcgtgtttac agtgcttaac cacattcgaa cataccaggc gaaagctctt acatacgcaa    1320
atgttttgtc ctttgtcgaa tcgattcgat cgagggtaat cattaacggt gtgacagcga    1380
```

-continued

```
ggtccgaatg ggatgtggac aaatctttgt tacaatcctt gtccatgacg ttttacctgc    1440
atactaagct tgccgttcta aaggatgact tactgattag caagtttagt ctcggttcga    1500
aaacggtgtg ccagcatgtg tgggatgaga tttcgctggc gtttgggaac gcatttccct    1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
ctgtggacat gcctgcgctt gacattagga agaagatgga agaaacggaa gtgatgtaca    1740
atgcactttc agagttatcg gtgttaaggg agtctgacaa attcgatgtt gatgtttttt    1800
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc tttggtagtt acctcaagag    1980
aagttgaaga accgtccatg aagggttcga tggccagagg agagttacaa ttagctggtc    2040
ttgctggaga tcatccggag tcgtcctatt ctaagaacga ggagatagag tctttagagc    2100
agtttcatat ggcaacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttaaaa cccacgcgag gaagtatcat gtggcgcttt    2400
tggaatatga tgagcagggt gtggtgacat gcgatgattg gagaagagta gctgtcagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
ggaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatcc    3120 tgactttac ccaatcggat aaagaagctc tgctttcaag agggtattca gatgttcaca    3180
ctgtgcatga agtgcaaggc gagacatact ctgatgtttc actagttagg ttaaccccta    3240
caccagtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat ttcattgaat gtcaaagatt    3600
gcatattgga tatgtctaag tctgttgctg cgcctaagga tcaaatcaaa ccactaatac    3660
ctatggtacg aacggcggca gaaatgccac gccagactgg actattggaa aatttagtgg    3720
```

-continued

```
cgatgattaa aaggaactttt aacgcacccg agttgtctgg catcattgat attgaaaata    3780
ctgcatcttt agttgtagat aagttttttg atagttattt gcttaaagaa aaagaaaac     3840
caaatataaaa tgtttctttg ttcagtagag agtctctcaa tagatggtta gaaaagcagg   3900
aacaggtaac aataggccag ctcgcagatt ttgattttgt agatttgcca gcagttgatc    3960
agtacagaca catgattaaa gcacaaccca agcaaaaatt ggacacttca atccaaacgg    4020
agtacccggc tttgcagacg attgtgtacc attcaaaaaa gatcaatgca atatttggcc    4080
cgttgtttag tgagcttact aggcaattac tggacagtgt tgattcgagc agatttttgt    4140
ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt tgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt ctttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagaggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt agttaatat tagaaatgtg     5340
aagatgtcag cgggtttctg tccgctttct ctggagtttg tgtcggtgtg tattgtttat   5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa agagtgatga tccgcaaagg gaaaaatagt    5580
agtaatgatc ggtcagtgcc gaacaagaac tatagaaatg ttaaggattt tggaggaatg    5640
agttttaaaa agaataattt aatcgatgat gattcggagg ctactgtcgc cgaatcggat    5700
tcgttttaaa tatgtcttac agtatcacta ctccatctca gttcgtgttc ttgtcatcag    5760
cgtgggccga cccaatagag ttaattaatt tatgtactaa tgccttagga aatcagtttc    5820
aaacacaaca agctcgaact gtcgttcaaa gacaattcag tgaggtgtgg aaaccttcac    5880
cacaagtaac tgttaggttc cctgacagtg actttaaggt gtacaggtac aatgcggtat    5940
tagacccgct agtcacagca ctgttaggtg cattcgacac tagaaataga ataatagaag    6000
ttgaaaatca ggcgaacccc acgactgccg aaacgttaga tgctactcgt agagtagacg    6060
acgcaacggt ggccataagg agcgcgataa ataatttaat agtagaattg atcagaggaa    6120
```

```
ccggatctta taatcggagc tctttcgaga gctcttctgg tttggtttgg acctctggtc    6180
ctgcaacttg aggtagtcaa gatgcataat aaataacgga ttgtgtccgt aatcacacgt    6240
ggtgcgtacg ataacgcata gtgttttttcc ctccacttaa atcgaagggt tgtgtcttgg   6300
atcgcgcggg tcaaatgtat atggttcata tacatccgca ggcacgtaat aaagcgaggg    6360
gttcgaatcc ccccgttacc cccggtaggg gccca                               6395
```

<210> SEQ ID NO 3
<211> LENGTH: 1245
<212> TYPE: DNA
<213> ORGANISM: Artificial Sequence
<220> FEATURE:
<223> OTHER INFORMATION: Description of Artificial Sequence: cDNA copy
      of the nucleotide sequence of the genome of STNV-2

<400> SEQUENCE: 3

```
agtaaagaca ggaaacttta ccgactatca gaatgacaaa acgtcaaagc aaacaatcaa     60
accgcaagag cgttgcatca caggtgcgta gtattgttga gtcaatggct gagcagaagc    120
gatttgcttt tcttacgaac accaacacag tcactacagc aggtaccgtg atcaacctga    180
gcaacaacat cgtgcaagga gatgaccttg ttaatcgcac cggagaccag attaagacca    240
tacaccagac tttattgact cggtgtacag gaattaccaa cagccaaagc tttcggttca    300
tctggtttcg tgacaacacc aataggggga ctacaccggc tgtgactgag gtgttagaca    360
gtgctagtat aacatcccag tataacccca ctacgttcca gcaaaagagg ttcactgttt    420
tccaagattt catgttggat acctctatag ttggacgtgt gattgtccat cggactgccg    480
ttgataagaa acggcgtgcg atattttaca acggtgctgc ttctgtagcc gcgtcaaatg    540
gccccggtgc cacatttgta cttgtcattg gatcacatgc cactggacag tatgatgtga    600
cagccgagat tgtttatctg gacatgtaga ccatggtcat gatgatgata gtgaaggacg    660
ctgaaagatg cgtagctacc ctcctggtgc acttcctggt gcaaagcaga accaaagggt    720
acggtggtac ggcggacagt agtcctgaac tagtaaatca ggaccgggag aaaaccagct    780
gacggctaaa tccattccca ctagtgtatt agtggaacga ggccccgcgt gaattggggt    840
ggctgcatgg ggtggaaaac catgtggtcg cagtcatttc tcctatgcat tattgtctca    900
atacttgtgt gcaacaatgc tgttaatcaa cgtagcactc aacatcactt caaaaccccc    960
tccatgtcac aagaatcaag atgcatgtct gtgtttagcg gtatatattt tgcatccact   1020
tgatcgtgat tttgccctgg gcacctcgcg cggttggtac ccgcggagac tccccacagc   1080
aacatggcat taggcaggga taaggtatag tgactagaca aatgcgcgtg aagctggaaa   1140
gtccggttag cagtggggtt gtgcggaatg cagcctcaac aaggtatagc tgctgcatag   1200
gagatgtgaa cctttcaaac ttgaattcaa gtctcatgac tgccc                   1245
```

<210> SEQ ID NO 4
<211> LENGTH: 1058
<212> TYPE: DNA
<213> ORGANISM: Artificial Sequence
<220> FEATURE:
<223> OTHER INFORMATION: Description of Artificial Sequence: cDNA copy
      of the nucleotide sequence of the genome of STMV <400> SEQUENCE: 4

```
agtaaactta ccaatcaaaa gacctaacca acaggactgt cgtggtcatt tatgctgttg      60
ggggacatag ggggaaaaca tattgccttc ttctacaaga ggccttcagt cgccataatt    120
```

-continued

| | |
|---|---|
| acttggcgcc caattttggg tttcagttgc tgtttccagc tatggggaga ggtaaggtta | 180 |
| aaccaaaccg taaatcgacg ggtgacaatt cgaatgttgt tactatgatt agagctggaa | 240 |
| gctatcctaa ggtcaatccg actccaacgt gggtcagagc catacctttc gaagtgtcag | 300 |
| ttcaatctgg tattgctttt aaagtaccgg tcgggtcact attttcggca aatttccgga | 360 |
| cagattcctt tacaagcgtc acagtgatga gtgtccgtgc ttggacccag ttaacaccgc | 420 |
| cagtaaatga gtacagtttt gtgaggctga agccattgtt caagactggt gactctactg | 480 |
| aggagttcga agggcgtgca tcaaacatca acacacgagc ttctgtaggg tacaggattc | 540 |
| caactaattt gcgtcagaat actgtggcag ccgacaatgt atgcgaagta agaagcaact | 600 |
| gtcgacaagt cgccttggtt atttcgtgtt gttttaactg aacctcgaca taagcctttt | 660 |
| ggatcgaagg ttaaacgatc cgctcctcgc ttgagcttga ggcggcgtat ctcttatgtc | 720 |
| aacagagaca ctttggtcta tggttgtata caatagata gactcccgtt tgcaagatta | 780 |
| gggttaacag atcttgccgt tagtctggtt agcgcgtaac cggccttgat ttatggaata | 840 |
| gatccattgt ccaatggctt tgccaatgga acgccgacgt ggctgtataa tacgtcgttg | 900 |
| acaagtacga aatcttgtta gtgttttttcc ctccacttaa atcgaagggt tttgttttgg | 960 |
| tcttcccgaa cgcatacgtt agtgtgacta ccgttgttcg aaacaagtaa aacaggaagg | 1020 |
| gggttcgaat ccctccctaa ccgcgggtaa gcggccca | 1058 |

<210> SEQ ID NO 5
<211> LENGTH: 6355
<212> TYPE: DNA
<213> ORGANISM: Artificial Sequence
<220> FEATURE:
<223> OTHER INFORMATION: Description of Artificial Sequence: cDNA copy
    of the nucleotide sequence of the genome of TMV-U2

<400> SEQUENCE: 5

| | |
|---|---|
| gatgttttaa tagttttcga caacaacaat taaaacaaaa acaacatatt acaaacaaca | 60 |
| aacaacaaca atggcacaca tacaatctat aattagcaac gcccttcttg aaagcgtgag | 120 |
| tggtaaaaac actctcgtta atgaccttgc aagaaggcgc atgtacgata cggccgtgga | 180 |
| agaatttaac gcccgcgacc gtagaccaaa ggtcaacttt tccaaaacta ttagcgaaga | 240 |
| gcaaacgctt ctagtctcca acgcgtaccc ggagttccag attaccttt ataatactca | 300 |
| aaatgccgta cacagtttgg ctggaggttt gagagcatta gaattggaat atctgatgct | 360 |
| acaagttccc tatggatcgc cgacatatga tataggtggg aactttgcag cacatttgtt | 420 |
| caaaggcagg gattacgtgc attgctgtat gcccaatctg acatacgag atataatgag | 480 |
| gcacgaagga caaaaggact caattgagat gtatttgtcc agattgtctc gttctaacaa | 540 |
| ggtaattcct gagtttcaaa gggaggcttt taacaggtat gcagaagctc ccaacgaagt | 600 |
| ctgctgctct aaaacttttc aggattgtcg aatacatccg ccagagaata gtggtagaag | 660 |
| atacgctgtt gctctgcaca gtttgtatga tattcctgtg catgagtttg gagctgcgtt | 720 |
| aatatctaag aatatacatg tatgttatgc agcttccatt ttggcagaag cattattact | 780 |
| agaccagacg gaggttacgc ttaatgaaat aggcgcaact ttcaaaagag aaggtgatga | 840 |
| tgtttctttt tttcttgctg atgaaagtac tttaaattat agtcataaat acaaaaatat | 900 |
| cttgcattat gtagttaaat cttactttcc tgcttctagt agaatagttt actttaagga | 960 |
| attttttagtc actagggtta atacttggtt ttgtaaattt accaaagtag ataccatat | 1020 |
| tctgtacaag agtgttagac aagtagggtg tgatagtgat cagttctatg aggcgatgga | 1080 |

```
agacgccttt gcttacaaga aaaccttggc catgttcaac actgaaagag caatctttag   1140
agacacggct tcggttaact tttggttccc taagatgaag acatggtga tagtaccgct    1200 gtttgagggt tctattacca gcaaaaagat gacaaggagt gaggtcattg ttaatcgtga   1260
cttcgtttac acagtgctta atcatatcag aacatatcaa gccaaagcgt taacttacca   1320
gaacgtatta tctttcgtgg agtctataag atcccgcgtg ataatcaatg gtgttactgc   1380
taggtctgaa tgggatgtag ataaagcaat tcttcaaccc ttgtcaatga ctttcttctt   1440
gcagactaag ctggctgcgc ttcaagacga tatagtaatg ggaaagtttc ggtgcttgga   1500
taagaccact tctgaactta tttgggatga ggtgggcaaa ttttttggaa cgttttccc    1560 cactatcaaa gagagattgg tgagcaggaa aattctggat gtaagtgaga atgctctgaa   1620
gatcaagatc ccagatctgt atgtcacatg gaaagacagg ttcgtagctg aatacaccaa   1680
gtctgaggag ttaccgcatc tagatatcaa gaaggactta aagaagctg agcaaatgta    1740 cgacgcgtta tcagaattat ctatccttaa gggtgctgat aatttcgata tcgcgaagtt   1800
caaagacatg tgcaaggctt tagatgttag tcctgatgtg gcagcacgag taatcgttgc   1860
agtggccgag aatagaagcg gtttaactct tacttttgat aagccaaccg aggagaatgt   1920
ggctaaggct cttaaaagca cggcgtctga ggccgtggta tgtcttgaac cgacatccga   1980
agaggtgaac gtaaataaat tttctattgc tgagaaaggg agattgcctg tgtgtgcaga   2040
aagtcatggt ttgacgaatg ctaacttaga gcaccaggag ttggagtccc tcaacgattt   2100
ccataaggct tgcgtggata gtgtgattac aaagcaaatg gcatcggttg tctacactgg   2160
ctcactcaaa gttcaacaaa tgaagaacta tgtggacagt ttggcagctt cgttgtccgc   2220
cactgtatca aatctatgca agtcactaaa ggatgaagtc gggtatgatt ctgattccag   2280
ggagaaagtt ggtgtttggg atgtcacttt gaaaaagtgg ctcctcaaac ctgcggccaa   2340
aggtcattca tggggagttg tcctggatta caaggggaaa atgtttactg cacttctatc   2400
ttatgaagga gatagaatgg tgactgagag cgactggagg agggtggctg tatcatctga   2460
tacaatggta tattctgata ttgcaaagct ccaaaatctg aggaaaacaa tgagagacgg   2520
tgaaccccac gaacctactg caaagatggt acttgtggat ggggtgcctg gttgtggaaa   2580
gtacaaagga gattttgaaa gatttgatct tgatgaggat ttgatcttgg ttcctggaaa   2640
acaagctgct gctatgatca gaagaagggc taattcatct ggactgataa gagccacaat   2700
ggacaatgtg agaacggtag attcacttct aatgcatcca aaaccgcgat cacacaagag   2760 gcttttttatt gatgaagggt tgatgctgca caccggttgt gttaacttcc tggtgcttat   2820
ctctggttgc gacatcgcat acatttacgg agatacacag cagattcctt tcattaacag   2880
agttcagaat ttcccgtatc ccaaacattt tgagaagctg caagtggatg aagttgagat   2940
gaggaggacc acactgagat gcccaggtga tgtgaatttt ttcctacaat cgaagtacga   3000
aggagcggtg acaaccactt caactgtaca acgatcggtc tcatctgaga tgataggcgg   3060
taagggagta ctaaacagtg tttccaaacc actaaagggg aaaattgtaa ctttcactca   3120
ggctgataaa tttgagttag aggagaaggg ctataagaat gtgaacaccg ttcatgagat   3180
ccaaggagaa acctttgaag atgtgtcgct ggtcagattg acggcaactc cactgactct   3240
gatttccaag tcttccccgc atgttctagt cgctctgact agacacacaa agagcttcaa   3300
atattacacc gtagtgttag atcctttagt acagataatt agtgatttgt cttctttaag   3360
ctccttcctt ttgaaaatgt atatggtaga agcaggtagt agatagcaat tacagatgga   3420
tgcagtgttc aaaggtcata atctctttgt ggcaacacct aaatcaggag actttccaga   3480
```

-continued

```
tctacagttc tattacgatg tatgcctccc tggtaatagt actatactta acaagtatga    3540
tgctgttacc atgaggttac gtgataatag tcttaatgtg aaggattgtg ttcttgattt    3600
ttccaaaagt attccgatgc caaaggaggt gaaaccatgt ctagagccag ttttgcgtac    3660
cgcggcggaa ccgccaaggg ctgcaggact actcgaaaat ctggttgcaa tgattaaaag    3720
aaatttcaac gcaccagacc tgacggggac gattgacatt gagagcaccg catctgttgt    3780
agtagataag ttttttgata gctattttat taaaaaagaa aaatacacaa aaatattgc    3840 tggagtgatg acgaaggatt caatgatgag atggttggaa acaggaaag aagtactatt    3900 ggacgacttg gctaactaca attttacaga tctgccggcc atcgatcagt acaagcacat    3960
gatcaaggct caaccaaaac agaaattgga cctttcaatt cagaatgaat accctgctct    4020
gcaaacaatt gtctaccatt cgaagcagat caacggtatt ttggccggtt tctcagagct    4080
tacaaggttg ctgctcgagg catttgattc taagaagttt cttttcttta ctaggaaaac    4140
tccagaacag attcaagaat ttttctcgga tctcgactcg cacgttccta tggatgtgtt    4200
agaactggat atttctaagt atgataagtc acagaacgag tttcattgtg ctgtagagta    4260
tgaaatatgg aaaagattgg gtctcaatga gttttttggcc gaagtgtgga aacaagggca    4320
caggaaaaca actttgaagg attacattgc tggaatcaag acatgtctgt ggtatcaaag    4380
gaaaagcggt gatgtgacta ctttcatcgg caatactgtt ataatagcag cttgcttggg    4440
ttcaatgtta ccgatggaaa aggtcataaa aggtgctttt tgtggagacg attccgtttt    4500
gtattttcca aagggtttgg atttccctga cattcagtca tgtgctaatc tcatgtggaa    4560
ttttgaggcc aaactgtata gaaagaggta cggttacttt tgtggtagat acatcataca    4620
ccatgataag ggagcaatag tgtattatga tcctttgaag ttgatctcca aacttggggc    4680
aaaacatatc aaggattatg atcacttaga agagttaagg gtgtctttgt gcgatgttgc    4740
ttgttcgctc ggaaactggt gcttaggctt ccgcagctg aacgcagcta tcaaggaggt    4800
tcataaaacc gcgattgatg gttcgtttgc ttttaattgt gttaacaaat tttgtgtga    4860 taaattttta tttagaactt tgtttttaaa tggctgttag tctcagagat actgtcaaaa    4920
ttagcgagtt cattgatctt tcgaaacagg atgagatact tccggcattc atgactaagg    4980
tcaagagtgt tagaatatcg actgtggaca agattatggc tgttaagaat gatagtcttt    5040
ctgatgtaga tttacttaaa ggtgttaagt tagttaagaa agggtatgtg tgcttagctg    5100
atttggtagt gtctggggag tggaatctcc cggataactg ccgtggtggt gtcagtgttt    5160
gtattgtaga taagagaatg aaaaggagta aggaagcaac gctgggtgcg tatcacgccc    5220
ctgcttgcaa aaagaatttt tcttttaagc taatccctaa ttattcaata acatccgagg    5280
atgctgagaa gcacccgtgg caagtgttag tgaatatcaa aggagtggct atggaagaag    5340
gatactgtcc tttatctttg gagttcgttt caatttgtgt agtacataaa aataatgtaa    5400
gaaaaggttt gagggaacgt attttgagtg tgacagacgg ctcgccaatt gaactcactg    5460
aaaaggttgt tgaggagttc gtggatgaag taccaatggc tgtgaaactc gaaaaggttc    5520
cggaaaacaa aaaagaaatg gtaggtaata atgttaataa taagaaaata ataacagtg    5580 gtaagaaggg ttttaaaatt gaggaaattg aggataatgt aagtgatgac gagtctatcg    5640
cgtcatcgag tacgttttaa tcaatatgcc ttatacaatc aactctccga gccaatttgt    5700
ttacttatct tccgcttacg cagatcctgt gcagctgatc aatctgtgta caaatgcatt    5760
gggtaaccag tttcaaacgc aacaagctag gacaacagtc caacagcaat ttgcggatgc    5820
```

| | |
|---|---|
| ctggaaacct gtgcctagta tgacagtgag atttcctgca tcggatttct atgtgtatag | 5880 |
| atataattcg acgcttgatc cgttgatcac ggcgttatta aatagctttg atactagaaa | 5940 |
| tagaataata gaggttgata atcaacccgc accgaatact actgaaatcg ttaacgcgac | 6000 |
| tcagagggta gacgatgcta ctgtagctat aagggcttca atcaataatt tggctaatga | 6060 |
| actggttcgt ggaactggca tgttcaatca agcaggcttt gagactgcta gtggacttgt | 6120 |
| ctggaccaca actccggcta cttagctatt gttgtgagat ttcctaaaat aaagtcgctg | 6180 |
| aagacttaaa attcagggtg gctgatacca aaatcagcag tggttgttcg tccacttaaa | 6240 |
| tataacgatt gtcatatctg gatccaacag ttaaaccatg tgatggtgta tactgtggta | 6300 |
| tggcgtaaaa catcggagag gttcgaatcc tcccctaacc gccggtagcg gccca | 6355 |

<210> SEQ ID NO 6
<211> LENGTH: 2346
<212> TYPE: DNA
<213> ORGANISM: Artificial Sequence
<220> FEATURE:
<223> OTHER INFORMATION: Description of Artificial Sequence: nucleotide
      sequence of the tomato phytoene desaturase (pds)
      encoding cDNA

<400> SEQUENCE: 6

| | |
|---|---|
| cttttactag ttatagcatt cggtatcttt ttctgggtaa ctgccaaacc accacaaatt | 60 |
| acaagtttcc atttaactct tcaacttcaa cccaaccaaa tttatttcct taattgtgca | 120 |
| gaaccactcc ctatatcttc taggtgcttt cattcgttcc gaggtaagaa agattttttg | 180 |
| tttctttgaa tgctttatgc cactcgttta acttctgagg tttgtggatc ttttaggcga | 240 |
| ctttttttt ttttgtatgt aaaatttgtt tcataaatgc ttctcaacat aaatcttgac | 300 |
| aaagagaagg aattttacca agtatttagg ttcagaaatg gataattttc ttactgtgaa | 360 |
| atatccttat ggcaggtttt actgttattt ttcagtaaaa tgcctcaaat tggacttgtt | 420 |
| tctgctgtta acttgagagt ccaaggtagt tcagcttatc tttggagctc gaggtcgtct | 480 |
| tctttgggaa ctgaaagtcg agatggttgc ttgcaaagga attcgttatg ttttgctggt | 540 |
| agcgaatcaa tgggtcataa gttaaagatt cgtactcccc atgccacgac cagaagattg | 600 |
| gttaaggact gggggccttt aaaggtcgta tgcattgatt atccaagacc agagctggac | 660 |
| aatacagtta actatttgga ggctgcattt ttatcatcaa cgttccgtgc ttctccgcgc | 720 |
| ccaactaaac cattggagat tgttattgct ggtgcaggtt tgggtggttt gtctacagca | 780 |
| aaatatttgg cagatgctgg tcacaaaccg atactgctgg aggcaaggga tgttctaggt | 840 |
| ggaaaggtag ctgcatggaa agatgatgat ggagattggt acgagactgg tttgcatata | 900 |
| ttctttgggg cttacccaaa tattcagaac ctgtttggag aattagggat taacgatcga | 960 |
| ttgcaatgga aggaacattc aatgatattt gcaatgccaa gcaagccagg agaattcagc | 1020 |
| cgctttgatt tctccgaagc tttacccgct ccttttaaatg gaatttttagc catcttaaag | 1080 |
| aataacgaaa tgcttacatg gccagagaaa gtcaaatttg caattggact cttgccagca | 1140 |
| atgcttggag ggcaatctta tgttgaagct caagatggga taagtgttaa ggactggatg | 1200 |
| agaaagcaag gtgtgccgga cagggtgaca gatgaggtgt tcattgctat gtcaaaggca | 1260 |
| ctcaacttta taaaccctga cgaactttca atgcagtgca ttttgatcgc attgaacagg | 1320 |
| tttcttcagg agaaacatgg ttcaaaaatg gcctttttag atggtaatcc tcctgagaga | 1380 |
| ctttgcatgc cgattgttga acacattgag tcaaaaggtg gccaagtcag actgaactca | 1440 |
| cgaataaaaa agattgagct gaatgaggat ggaagtgtca gagtttttat actgagtgac | 1500 |

-continued

```
ggtagtgcaa tcgagggaga tgcttttgtg tttgccgctc cagtggatat tttcaagctt    1560
ctattgcctg aagactggaa agagattcca tatttccaaa agttggagaa gttagtcgga    1620
gtacctgtga taaatgtaca tatatggttt gacagaaaac tgaagaacac atatgatcat    1680
ttgctcttca gcagaagctc actgctcagt gtgtatgctg acatgtctgt tacatgtaag    1740
gaatattaca accccaatca gtctatgttg gaattggttt ttgcacctgc agaagagtgg    1800
atatctcgca gcgactcaga aattattgat gcaacgatga aggaactagc aacgcttttt    1860
cctgatgaaa tttcagcaga tcaaagcaaa gcaaaaatat tgaagtacca tgttgtcaaa    1920
actccgaggt ctgtttataa aactgtgcca ggttgtgaac cctgtcggcc tttacaaaga    1980
tccccaatag gggggtttta tttagccggt gactacacga aacagaaata cttggcttca    2040
atggaaggcg ctgtcttatc aggaaagctt tgtgctcaag ctattgtaca ggattatgag    2100
ttacttgttg gacgtagcca aaagaagttg tcggaagcaa gcgtagttta gctttgtggt    2160
tattatttag cttctgtaca ctaaatttat gatgcaagaa gcgttgtaca caacatatag    2220
aagaagagtg cgaggtgaag caagtaggag aaatgttagg aaagctccta tacaaaagga    2280
tggcatgttg aagattagca tcttttttaat cccaagttta aatataaagc atattttatg    2340
gaattc                                                              2346
```

<210> SEQ ID NO 7
<211> LENGTH: 7096
<212> TYPE: DNA
<213> ORGANISM: Artificial Sequence
<220> FEATURE:
<223> OTHER INFORMATION: Description of Artificial Sequence: nucleotide
      sequence of the tobacco nitrate reductase (nia-2)
      encoding cDNA

<400> SEQUENCE: 7

```
tacatacaag ggcgcgaata aacttttttt aaagtaaatg tatatgaact tgcaatgaaa      60 gaggaccttta acttgtttgt ctttgttgct ttctgcaaat ttcaccttaa cagcccattt     120
gagattgatt tagttagtta taacaattag ttaaatgctt gtgtaatttg aagaaaatat     180
ttggacgtgc tcgctgaaaa cattatactc ctatataata gaaatacttt ctgaaaagtt     240
ggtcttgttc aaaaacgtat aagagagttg gtcttctcat aaatagtcac tagctttctg     300
attttttttc actttctata tcacgtaaat aggtactcaa atttgatatt tacaccaaac     360
aaatgaaaat aggatatgtg ttttttcatac gtatatttat ctatcgtact taatgataca     420
tacatataca tataacctta cttttttgatt actaaaaatt taattatatt taatttgggt     480
aaatatcaga tgccacaaaa catttaccta gccactgttt ttgactacta aaaatttaat     540
tatgtttagc ttgggtaaat atcagatgtc actaaacatt ttacctagcc attcctccga     600
aaagaaattg agaaggaaat tagagttagt ggagccataa taatgtttaa tgtgaccata     660
actcggtgaa aaccacggca agaataagaa acagctgtta aggctaacca acagctgcat     720
atctttaagc catttgctat taccccaaca tcgcatcttc ctctgatccc gaccctacgg     780
gcgtaaaaag tgtaaatcgt tagaattgtt ttatttattt tatgatgtca ctatttttta     840
aaatcaaaat taaattgggg tgtcgatttt tttgggtcct gcttatgtat agtatggcgc     900
tatggaggca ctgagagagt ccgaaacgtt tctatataag gccaccccac gcattcacaa     960
acttcgttcc caaacagaac aagaaaatca aatctcggag agagagagag agaaatattt    1020
tgagagagaa atacagaaaa tctctcttcc ttctttcctt tttttttcaa tccccattca    1080
```

-continued

| | |
|---|---|
| tattcttttt ttagaataat ctatggcggc atctgtcgaa aacaggcagt tcagtcacct | 1140 |
| agaagccggt ttatcccggt cttcaagcc ccggtctgat tccccggttc gtggctgcaa | 1200 |
| cttcccttcg cccaacagta ctaatttcca aagaaacca aattccacca tttaccttga | 1260 |
| ttactcgtcg agtgaagacg acgatgatga tgacgaaaaa aatgagtacc ttcaaatgat | 1320 |
| taaaaagggg aattcagagt tagagccatc tgttcatgac actagggacg aaggtaccgc | 1380 |
| tgataattgg attgaacgca acttttccat gattcgtctc accggaaagc atccatttaa | 1440 |
| ctccgaacca ccgttgaacc ggctcatgca ccacggcttt atcacaccgg tcccacttca | 1500 |
| ttacgttcgt aaccatggac cggttcccaa gggcacgtgg gatgactgga ccgtggaagt | 1560 |
| cacgggacta gtgaagcgtc ctatgaaatt cacaatggac cagttggtta acgaattccc | 1620 |
| ttgtagagaa ttgcccgtta cgcttgtttg tgctggcaat cgaaggaaag aacagaacat | 1680 |
| ggttaaacaa accattggtt tcaactgggg cgccgctgcc gtttcaacaa cgatatggcg | 1740 |
| cggggtaccc ctccgcgctt tgctaaaacg gtgcggtgtt tttagcaaga ataaaggggc | 1800 |
| gcttaatgtt tgcttcgaag gagctgatgt gttgcccgga ggtggtggtt caaagtatgg | 1860 |
| aaccagcatt aagaaggaat tgcaatggga tccagcacga gatatcatcg tagcctacat | 1920 |
| gcagaacgga gaaaaattgg cacccgacca cgggtttcca gtacgaatga taattccagg | 1980 |
| attcattgga ggaagaatgg tgaaatggat aagaggatt atagtcacca cccaagaatc | 2040 |
| agacagctat tatcatttca aggacaatag agttcttcct ccccatgttg atgctgaact | 2100 |
| tgcaaatacc gaaggtacgt accgtaacta tttcaattta ttactccatt tgttccaatt | 2160 |
| tatgtgaacc tatttccttt ttggtccgtt caaaaaagaa tgaaccctt ctaaatttgg | 2220 |
| taacaattta gcttaaactt acaacttcac ccttaatgag aaactttat aaccacacaa | 2280 |
| ataccctggg gcccatttgg acttgtttag gtcgacaaat tccaaaagtt ttatttttt | 2340 |
| cttaaacttc gtgctcagtc aaacaggttc acgtaaattg aaacggagag agtatcattt | 2400 |
| ttattaaggg gtataaatat atttaatta gttgagactt gcacatacaa gtaaaatatt | 2460 |
| tcttagaata caaaatcaac tgaaagctta cttctaatta tatggttttg aattttcctt | 2520 |
| tcaatgaagt aaataaaaag gaaacaatta tattcaacgc atgtaggtat atggtcctgt | 2580 |
| cattatctca aatcaaatgg tttaaagaca aaggactttg gaaacataga attgtcagct | 2640 |
| ttatagttat ggagtactat attagttagc tgtttgcatc tattcataat tggtctatct | 2700 |
| gtgtgcagca tggtggtaca agccagagta tatcatcaat gagcttaata ttaactctgt | 2760 |
| cattacgacg ccgtgtcatg aagaaatttt gccaattaac gcctggacga ctcagcgacc | 2820 |
| ttacacgttg aggggctatt cttattctgg ttagtatttt tatattttcc gattttgctg | 2880 |
| agaatatcat atttcttagt tttgtcgata catcgtatcc tctaactctg acgttttact | 2940 |
| tcgtccttat gcacccactt acgtccttac tttctcagac agtttattga tgaaaactac | 3000 |
| ttactatttt cgacccgata gcctcagcgt ccttaattaa atgtgatgtt ttgaaagaga | 3060 |
| tattctctcc cgtctatttt aattaatttt tggctgtttt tatacgtggg aatctatttt | 3120 |
| taacattaat taatatagaa atgaaccata ttaatattat taatttcttc attgaaaata | 3180 |
| caacaaatac tcttcggctc ttactacaat gacaattttg aagaaaaata attaattcct | 3240 |
| tcctaatatc tgaaaaatca atattgtgg accataaaaa aaggtcaaaa aattaattaa | 3300 |
| aatgaactgg agagagtaaa ttagaaaata taattatagc actagtaatt aaagttatta | 3360 |
| gatgtcttct ttaaaaagcg tgtgaaaact ttaaagacga aatataatat gaatattatc | 3420 |
| taatacttag aaagtgtcaa taattggtag acaatttaaa ctatatacta gttaaaaagt | 3480 |

-continued

```
ctgtcaatac aactattagt attggggatt agagagaata gtagtaaaat ggagtaattg      3540
gacgcatgag cttgggcatg ctgattgctg tcagcttgtt tgctaatgtg aaaagaaaa       3600 tagtaagaaa aggccaacat ggttttgttt attttattat gtggtagtac acaaaaacct      3660
ggggagcttt cctagttctg aagagtcggt ctttggtagc acaaaattaa tagtatagta      3720
taccaagtga atattaaatt caattgtcta agcacggaa tcttttttgac tactttagtt      3780 cctgcatctt gggttgcctc aacaacaccc tttattgaat tattatagta atgttcaata      3840
taatatacaa ttagaaaaca ctctaagtgg tcactttata tggatctagt caatactatt      3900
tcttctaaac aacgtgccta attacttccc actttccagt acatgaccac cattaagttt      3960
aatttttgtc aattccttgt gcaattggcc cttcaaatga gcagaagtgt tacgtaggaa      4020
aactaacttc agctactatt ataggagtaa acctgttagg aaaagatgct cgaggaactg      4080
acaaaacttg tagaataatt agccattgta ttgattgaaa tactgattgt gaacgtgtaa      4140
caaacaggcg gagggaaaaa agtaacgcga gtagaagtga cgttggatgg aggagaaaca      4200
tggcaagtta gcacactaga tcacccagag aagcccacca aatatggcaa gtactggtgt      4260
tggtgctttt ggtcactcga ggttgaggtg ttagacttgc tcagtgctaa agaaattgct      4320
gttcgagctt gggatgagac cctcaatact caacccgaga agcttatttg aacgtcatg       4380 gtacgttcac ttcttctttt acctttattt cttttaactt ctatatacta gcggtgtaaa      4440
gttattttac accataagtt aacttacaaa aatatgtaac tatttatact acgagtgatg      4500
agggcaagaa ggggtttaag tatttgacaa taaatgtaaa ccctgcaatt tgttcctaa       4560 tttttttatcc tttcaactct ttgtgattgc ttcattatct agattcacag agcacatgtg     4620
ttcacatgcc aaaacaaaaa actacaaaca aaaaacttt tcactagctt tagtctaaga      4680 ttccccttttt tttttttggg aggtgtgtgg tccatactcc atagatcaat tccagccact     4740
gacgtaccaa accctgaaaa ttcctagtag ttatagcgac gtacaatcat ttcatattat      4800
gtaagcagag acgtgatcac atgaactaga tgtgaatacc acttgcccag tccaccaggt     4860
caattcatct agatgtgtaa atcttgacac cagcactggg tcacttttat aacactagca     4920
tttaacaaca tttcatcctt gaacattact tgggctaatt aataagtatt tttttttata     4980
tactctaaaa attgtaatta cataaatgaa tttaacttat acacgctgac aatgttacta     5040
attccacttt ttacggacgg ttatctatag aaatcattta ggtgaaacaa ttctcttaca     5100
ctatgatcag tgttagtaca taatggttat tacattttct aaatattgtg ctatgttgca     5160
atgttcaggg aatgatgaat aattgctggt tccgagtaaa gatgaatgtg tgcaagcctc     5220
acaaggagga gattggaata gtgtttgagc atccgactca acctggaaac caatcaggtg     5280
gatggatggc gaaggagaga catttggaga tatcagcaga ggcacctcaa acactaaaga     5340
agagtatctc aactccattc atgaacacag cttccaagat gtactccatg tccgaggtca     5400
ggaaacacag ctctgctgac tctgcttgga tcatagtcca tggtcatatc tatgacgcca     5460
cgcgtttctt gaaagatcac cctggtggga ctgacagcat tctcatcaat gctggcactg     5520
attgcactga ggaatttgat gcaattcatt ctgataaggc taagaagctc ttggaggatt     5580
tcaggattgg tgaactcata actactggtt acacctctga ctctcctggc aactccgtgc     5640
acggatcttc ttccttcagc agctttctag cacctattaa ggaacttgtt ccagcgcaga     5700
ggagtgtggc cctaattcca agagagaaaa tcccatgcaa actcatcgac aagcaatcca     5760
tctcccatga tgttaggaaa tttcgatttg cattgccctc tgaggatcaa gtcttgggct     5820
```

-continued

```
tgcctgttgg aaaacatatc ttcctctgtg ccgttattga cgataagctc tgcatgcgcg    5880
cttacacgcc tactagcacg atcgatgagg tggggtactt cgagttggtt gtcaagatat    5940
acttcaaagg aattcaccct aaattcccca atggagggca aatgtcacag tatcttgatt    6000
ctatgccgtt agggtcattt ctcgacgtga aaggtccatt aggtcacatt gaataccaag    6060
gaaagggaaa tttcttagtt catggcaaac agaagtttgc caagaagttg gccatgatag    6120
caggtggaac aggaataact ccagtgtatc aagtcatgca ggcaattctg aaagatccag    6180
aagatgacac agaaatgtat gtggtgtatg ctaacagaac agaggatgat attttactta    6240
aggaagagct tgattcatgg gctgagaaaa ttccagagag ggttaaagtt tggtatgtgg    6300
ttcaggattc tattaaagaa ggatggaagt acagcattgg ttttattaca gaagccattt    6360
tgagagaaca tatccctgag ccatctcaca acaactggc tttggcttgt ggaccacctc     6420
ctatgattca atttgctgtt aatccaaact tggagaagat gggctatgac attaaggatt    6480
ccttattggt gttctaattt taaaaacaaa acaatatctg caggaataaa ttttttttt     6540 cccctatca gttgtacata ttgtatttgg tttatcaccc ccatgtacta cgtagtgttt     6600
gtagttctta cattttatt ttttagaatt ttttttaaacc ttaggatata aaggttttct    6660
cttccaacaa agtgattctt tagggaagaa atgtactgta ctgtactagt atgtctaagc    6720
cgaaagttgt aatgtttacc atgacaaatt gtattcaatt cctcatggaa tagtaacatt    6780
gtgttcatgt gtcttcctgt aagcgatctt caaaatatca atgtatatat atagtaattg    6840
caaaccattg ttccttttcc cgatgtagtt aactactctt tctttagctt ctagtctctg    6900
gtgaatattt tttttctat aactctttaa ttaatacggc cttaaataag agaaaagttt     6960
aaaccacgaa tatcattatg cagacgtata ggtaattaat ctacttttg aaaaaaaatc     7020 tattttcttt atgtggtcct tcaaaataat attctagaac cttttgtata ttccctttta    7080
acttctattt agtttt                                                    7096
```

<210> SEQ ID NO 8
<211> LENGTH: 1839
<212> TYPE: DNA
<213> ORGANISM: Artificial Sequence
<220> FEATURE:
<223> OTHER INFORMATION: Description of Artificial Sequence: nucleotide sequence of the tobacco nitrite reductase (nir-1) encoding cDNA

<400> SEQUENCE: 8

```
tttctattaa atttctggca ccttcattgc caaatccagc tagattttcc aagaatgctg      60
tcaagctcca cgcaactccg ccgtctgtgg cagcgccgcc agctggtgct ccagaggttg     120
ctgctgagag gctagaaccc agagttgagg aaaagatgg ttattggata ctcaaggagc      180
agtttagaaa aggcataaat cctcaagaaa aggtcaagat tgagaagcaa cctatgaagt     240
tgttcatgga aaatggtatt gaagagcttg ctaagatacc cattgaagag atagatcagt     300
ccaagcttac taaggatgat attgatgtta ggcttaagtg gcttggcctc ttccatagga     360
gaaagaacca atatgggcgg ttcatgatga gattgaagct tccaaatgga gtaacaacga     420
gtgcacagac tcgatacttg gcgagtgtga taggaaaata cgggaaagaa ggatgtgctg     480
atattacaac gaggcaaaat tggcagattc gtggagttgt actgcctgat gtgcccgaga     540
tactaaaggg actagcagaa gttgggttga ccagtttgca gagtggcatg acaatgtca     600 ggaatccagt aggaaatcct cttgctggaa ttgatccaga agaaatagta gacacagggc     660
cttacactaa tttgctctcc caatttatca ctggcaattc acgaggcaat cccgcagttt    720
```

| | |
|---|---|
| ctaacttgcc aaggaagtgg aatccgtgcg tagtaggctc tcatgatctt tatgaacatc | 780 |
| cccatatcaa cgatctcgcg tacatgcctg ccacgaaaga tggacgattt ggattcaacc | 840 |
| tgcttgtggg tgggttcttc agcgcaaaaa gatgtgatga ggcaattcct cttgatgcat | 900 |
| gggttccagc tgatgatgtt gttccggttt gcaaagcaat actggaagct tttagagatc | 960 |
| ttggtttcag agggaacaga cagaaatgta gaatgatgtg gttaatcgat gaactgggtg | 1020 |
| tagaaggatt cagggcagag gtcgagaaga gaatgccaca gcaagagcta gagagagcat | 1080 |
| ctccagagga cttggttcag aaacaatggg aagaagaga ttatcttggt gtacatccac | 1140 |
| aaaaacaaga aggctacagc tttattggtc ttcacattcc agtgggtcgt gttcaagcag | 1200 |
| acgatatgga tgagctagct cgtttagctg atgagtatgg ttcaggagag atccggctta | 1260 |
| ctgtggaaca aaacattatt attcccaaca ttgagaactc aaagattgag gcactgctca | 1320 |
| aagagcctgt tctgagcaca ttttcacctg atccacctat tctcatgaaa ggtttagtgg | 1380 |
| cttgtactgg taaccagttt tgtggacaag ccataatcga gactaaagct cgttccctga | 1440 |
| tgataactga gaggttcaa cggcaagttt ctttgacacg gccagtgagg atgcactgga | 1500 |
| caggctgccc gaatacgtgt gcacaagttc aagttgcgga cattggattc atgggatgcc | 1560 |
| tgactagaga taagaatgga aagactgtgg aaggcgccga tgttttctta ggaggcagaa | 1620 |
| tagggagtga ttcacatttg ggagaagtat ataagaaggc tgttccttgt gatgatttgg | 1680 |
| taccacttgt tgtggactta ctagttaaca actttggtgc agttccacga gaaagagaag | 1740 |
| aaacagaaga ctaataaaat ttagaatagt tggtgatttt gctgtgttca taacatgtaa | 1800 |
| tgtatgataa atcaatgcaa acatttctac ctacgtgag | 1839 |

<210> SEQ ID NO 9
<211> LENGTH: 1294
<212> TYPE: DNA
<213> ORGANISM: Artificial Sequence
<220> FEATURE:
<223> OTHER INFORMATION: Description of Artificial Sequence: cDNA of the beta-1,3-glucanase of Nicotiana plumbagenifolia

<400> SEQUENCE: 9

| | |
|---|---|
| ttgctcttca aatggctgct attatactgc taggattgct tgtttccagc actgagatag | 60 |
| taggagctca atcagtaggt gtttgctacg gaatgctggg caacaacttg ccaccagcat | 120 |
| cacaagttgt acaactgtac aagtcaaaaa acataagaag aatgaggctt tatgatccaa | 180 |
| atcaagcagc tttacaggct ttaagaggct ccaacattga agttatgtta ggagttccca | 240 |
| attcagatct ccaaaacatt gctgctaacc cctcaaatgc aaataattgg gtccagagga | 300 |
| atgtcagaaa tttctggcca gccgttaaat ttaggtacat tgccgttgga aatgaagtca | 360 |
| gccctgtaac aggcacatct tcacttaccc gatatcttct tccggccatg aggaacattc | 420 |
| ggaatgcgat ttcttcagca ggtttgcaaa acaatatcaa agtctcaagt tctgtagaca | 480 |
| tgaccttgat tgggaactct tttccaccat cacagggttc gtttaggaac gacgttaggt | 540 |
| cgttcattga tccgattatt gggtttgtaa ggcgcataaa ttcgccttta ctcgttaaca | 600 |
| tttatcctta ttttagctat gctggtaatc cgcgcgatat ttctctcccc tatgctcttt | 660 |
| tcactgctcc aaatgtggtg gtacaagatg gttcacttgg atatagaaac ttatttgatg | 720 |
| caatgtcgga tgctgtgtat gctgccctgt ctcgagccgg aggggctcg atagagattg | 780 |
| ttgtgtccga gagtggctgg ccatctgctg gcgcatttgc cgcgacaaca aacaatgcag | 840 |
| caacttacta caagaactta attcagcatg ttaaagggg tagtccaaga aggcctaata | 900 |

```
aagtcattga gacctatttta tttgctatgt ttgatgagaa taacaaaaac cctgaattgg    960
agaaacattt tggactcttt tcccccaaca agcagcccaa atatccactc agctttgggt   1020
tttcagatag atattgggac atttctgctg aaaataatgc tactgcagct tctctcataa   1080
gtgagatgtg ataagagagt tctctttaaa tatctttaca tggatggaaa acttagtacc   1140
aataactaga ttgtttcttt ctttatgcaa ttttcttgta atgagagact agtacttgct   1200
ctctgtgtcc ttgtggagag taactagaga caaattaagc aaataacata ataattgag   1260 tgttgattct gcaatgataa atagaaaaaa aaaa                               1294
```

<210> SEQ ID NO 10
<211> LENGTH: 720
<212> TYPE: DNA
<213> ORGANISM: Artificial Sequence
<220> FEATURE:
<223> OTHER INFORMATION: Description of Artificial Sequence: green
      fluorescent protein encoding regon

<400> SEQUENCE: 10

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 11
<211> LENGTH: 1809
<212> TYPE: DNA
<213> ORGANISM: Artificial Sequence
<220> FEATURE:
<223> OTHER INFORMATION: Description of Artificial
      Sequence:beta-glucuronidase encoding region

<400> SEQUENCE: 11

```
atggtccgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa   120
gaaagccggg caattgctgt gccaggcagt tttaacgatc agttcgccga tgcagatatt   180
cgtaattatg cgggcaacgt ctggtatcag cgcgaagtct ttataccgaa aggttgggca   240
ggccagcgta tcgtgctgcg tttcgatgcg gtcactcatt acggcaaagt gtgggtcaat   300
aatcaggaag tgatggagca tcagggcggc tatacgccat ttgaagccga tgtcacgccg   360
tatgttattg ccgggaaaag tgtacgtatc accgtttgtg tgaacaacga actgaactgg   420
cagactatcc cgccgggaat ggtgattacc gacgaaaacg gcaagaaaaa gcagtcttac   480
ttccatgatt tctttaacta tgccggaatc catcgcagcg taatgctcta caccacgccg   540
```

```
aacacctggg tggacgatat caccgtggtg acgcatgtcg cgcaagactg taaccacgcg      600
tctgttgact ggcaggtggt ggccaatggt gatgtcagcg ttgaactgcg tgatgcggat      660
caacaggtgg ttgcaactgg acaaggcact agcgggactt tgcaagtggt gaatccgcac      720
ctctggcaac cgggtgaagg ttatctctat gaactgtgcg tcacagccaa aagccagaca      780
gagtgtgata tctacccgct tcgcgtcggc atccggtcag tggcagtgaa gggcgaacag      840
ttcctgatta accacaaacc gttctacttt actggctttg gtcgtcatga agatgcggac      900
ttacgtggca aaggattcga taacgtgctg atggtgcacg accacgcatt aatggactgg      960
attgggccca actcctaccg tacctcgcat taccottacg ctgaagagat gctcgactgg     1020
gcagatgaac atggcatcgt ggtgattgat gaaactgctg ctgtcggctt taacctctct     1080
ttaggcattg gtttcgaagc gggcaacaag ccgaaagaac tgtacagcga agaggcagtc     1140
aacggggaaa ctcagcaagc gcacttacag gcgattaaag agctgatagc gcgtgacaaa     1200
aaccacccaa gcgtggtgat gtggagtatt gccaacgaac cggatacccg tccgcaagtg     1260
cacgggaata tttcgccact ggcggaagca acgcgtaaac tcgacccgac gcgtccgatc     1320
acctgcgtca atgtaatgtt ctgcgacgct cacaccgata ccatcagcga tctctttgat     1380
gtgctgtgcc tgaaccgtta ttacggatgg tatgtccaaa gcggcgattt ggaaacggca     1440
gagaaggtac tggaaaaaga acttctggcc tggcaggaga aactgcatca gccgattatc     1500
atcaccgaat acggcgtgga tacgttagcc gggctgcact caatgtacac cgacatgtgg     1560
agtgaagagt atcagtgtgc atggctggat atgtatcacc gcgtctttga tcgcgtcagc     1620
gccgtcgtcg gtgaacaggt atggaatttc gccgattttg cgacctcgca aggcatattg     1680
cgcgttggcg gtaacaagaa agggatcttc actcgcgacc gcaaaccgaa gtcggcggct     1740
tttctgctgc aaaaacgctg gactggcatg aacttcggtg aaaaaccgca gcagggaggc     1800
aaacaatga                                                             1809

<210> SEQ ID NO 12
<211> LENGTH: 411
<212> TYPE: DNA
<213> ORGANISM: Artificial Sequence
<220> FEATURE:
<223> OTHER INFORMATION: Description of Artificial Sequence: cDNA copy
      of part of the region of a TMV-U2 variant comprising
      the origin of assembly

<400> SEQUENCE: 12
ccctcgccaa ttgaactcac tgaaaaagtt gttgatgagt tcgtagatga agtaccgatg       60
gctgtgaaac tcgaaaggtt ccggaaaaca aaaagagag tggtaggtaa taatgttaat      120
aataagaaaa taaataatag tggtaagaag ggtttgaaag ttgaggaaat tgaggataat      180
gtaagtgatg acgagtctat cgcgtcatcg agtacgtttt aatcaatatg ccttatacaa      240
tcaactctcc gagccaattt gttttacttaa gttccgctta tgcagatcct gtgcagctga      300
tcaatctgtg tacaaatgca ttaggtaacc agtttcaaac gcaacaagct aggacaacag      360
tccaacagca atttgcggat gcctggaaac ctgtgcctag tatgacagtg a               411

<210> SEQ ID NO 13
<211> LENGTH: 198
<212> TYPE: DNA
<213> ORGANISM: Artificial Sequence
<220> FEATURE:
<223> OTHER INFORMATION: Description of Artificial Sequence: cDNA copy
      of STMV leader region
```

```
<400> SEQUENCE: 13
agtaaaactt accaatcaaa agacctaacc aacaggactg tcgtggtcat ttatgctgtt      60
gggggacata gggggaaaac atattgcctt cttctacaag aggccttcag tcgccataat     120
tacttggcgc ccaattttgg gtttcagttg ctgtttccag ctatggggag aggtaaggtt     180
aaaccaaacc gtaaatcg                                                   198

<210> SEQ ID NO 14
<211> LENGTH: 455
<212> TYPE: DNA
<213> ORGANISM: Artificial Sequence
<220> FEATURE:
<223> OTHER INFORMATION: Description of Artificial Sequence:cDNA copy of
      STMV trailer region

<400> SEQUENCE: 14
gacaagtcgc cttggttatt tcgtgttgtt ttaactgaac ctcgacataa gccttttgga      60
tcgaaggtta aacgatccgc tcctcgcttg agcttgaggc ggcgtatctc ttatgtcaac     120
agagacactt tggtctatgg ttgtataaca atagatagac tcccgtttgc aagattaggg     180
ttaacagatc ttgccgttag tctggttagc gcgtaaccgg ccttgattta tggaatagat     240
ccattgtcca atggctttgc caatggaacg ccgacgtggc tgtataatac gtcgttgaca     300
agtacgaaat cttgttagtg tttttccctc acttaaatc gaagggtttt gttttggtct      360
tcccgaacgc atacgttagt gtgactaccg ttgttcgaaa caagtaaaac aggaagggg      420 ttcgaatccc tccctaaccg cgggtaagcg gccca                                455

<210> SEQ ID NO 15
<211> LENGTH: 1971
<212> TYPE: DNA
<213> ORGANISM: Artificial Sequence
<220> FEATURE:
<223> OTHER INFORMATION: Description of Artificial Sequence: cDNA copy
      of part of the genome of a TMV-U1 variant, comprising
      MP and CP genes

<400> SEQUENCE: 15
ggaaacactg tgattatagc tgcatgtttg gcctcgatgc ttccgatgga gaaataatc       60 aaaggagcct ttgtggtga cgatagtctg ctgtacttcc caaagggttg tgagtttccg     120
gatgtgcaac actccgcgaa tcttatgtgg aatttttgaag caaaactgtt taaaaaacag   180
tatggatact tttgcggaag gtatgtaata catcacgaca gaggatgcat tgtgtattac    240 gatccccta agttgatctc gaaacttggt gctaaacaca tcaaggattg gaacacttg      300 gaggagttca gaaggtctct ttgtgatgtt gctgtttcgt tgaacaattg tgcgtattac   360
acacagttgg acgacgctgt atgggaggtt cataagaccg cccctccagg ttcgtttgtt  420
tataaaagtc tggtgaagta tttgtctgat aaagttcttt ttagaagttt gtttatagat  480
ggctctagtt gttaaaggaa aagtgaatat caatgagttt atcgacctga caaaaatgga  540
gaagatctta ccgtcgatgt ttaccccctgt aaagagtgtc atgtgttcca agttgataa   600 aataatggtt catgagaatg agtcattgtc agaggtaaac cttctcaaag gagttaagct  660
tattgatagt ggatacgtct gtttagccgg tttggtcgtc acgggcgagt ggaacttgcc  720
tgacaattgc agaggagtg tgagcgtgtg tctggtggac aaaaggatgg aaagagccga  780
cgaggccact ctcggatctt actacacagc agctgcaaag aaaagatttc agttcaaggt   840
cgttcccaat tatgctataa ccaccccagga cgcgatgaaa acgtctggc aagtttttagt    900
```

-continued

```
caatattaga aatgtaaaga tgtcagcggg tttctgtccg ctttctctgg agtttgtgtc      960
ggtgtgtatc gtttatagaa ataatataaa attaggtttg agagagaaga tcacaagtgt     1020
gagagatgga gggcccatgg aacttacaga agaagttgtt gatgagttca tggaagatgt     1080
ccctatgtca atcaggcttg caaagtttcg atctcgaacc ggaaaaaaga gtgatgtccg     1140
taaagggaaa attagtagta gtgatcggtc agcgccgaac aagaactata gaaatgttaa     1200
ggattttgga ggaatgagtt ttaaaaagaa taatttaatc gatgatgatt cggagactac     1260
tgtcgccgaa tcggattcgt tttaaatatg tcttacagta tcactactcc atctcagttc     1320
gtgttcttgt cagcagcgtg ggccgaccca atagagttaa ttaatttatg tactaatgcc     1380
ttaggaaatc agtttcaaac acaacaagct cgaactgtcg ttcaaagaca attcagtgag     1440
gtgtggaaac cttcaccaca agtgactgtt aggttccctg acagtgactt taaggtgtac     1500
aggtacaatg cggtattaga cccgctagtc acagcactgt taggtgcatt tgacactaga     1560
aatagaataa tagaagttga aaatcaggcg aaccccacaa ctgccgaaac gttagatgct     1620
actcgtagag tagacgacgc aacggtggcc ataaggagcg ctataaataa tttagtagta     1680
gaattgatca gaggaaccgg atcttataat cggagctctt tcgagagctc ttctggtttg     1740
gtttggaact ctggtcctgc aacttgaggt agtcaagatg cataataaat aacggattgt     1800
gtccgtaatc acacgtggtg cgtacgataa cgcatagtgt ttttccctcc acttaaatcg     1860
aagggttgtg tcttggatcg cgcgggtcaa atgtatatgg ttcatataca tccgcaggca     1920
cgtaataaag cgagggggttc gaatccccccc gttaccccccg gtagggggccc a          1971
```

What is claimed is:

1. A method for identifying a peptide-peptide interaction comprising:
   (a) providing a first fusion construct comprising target peptide of 8 to 15 residues fused to a first DNA binding domain (DBD);
   (b) providing a second fusion construct comprising a library encoded peptide (LEP) of 5 to 50 residues fused to second DBD, wherein said second DBD works as a complex with said first DBD to facilitate binding of said complex to a prokaryotic operator region;
   (c) contacting said first and second fusion constructs in a prokaryotic host cell which comprises said prokaryotic operator region, wherein said prokaryotic operator region is operationally linked to a coding region for one or more indicator polypeptides; and
   (d) determining binding of said complex to said operator region,
   whereby binding of said complex to said operator region identifies said LEP as a binding partner for said target peptide.

2. The method of claim 1, wherein binding of said complex to said operator acts to block the transcription of said coding region.

3. The method of claim 1, wherein said one or more indicator polypeptides render said prokaryotic host cell insensitive to phage infection.

4. The method of claim 3, wherein step (d) comprises infection with a phage that infects, replicates and lyses said prokaryotic host cell.

5. The method of claim 4, wherein said operator is the lacZ operator, and the first and second DBDs are derived from the λ repressor.

6. The method of claim 1, wherein one or more indicator polypeptides produce a colorimetric or fluorescent product.

7. The method of claim 1, wherein said one or more indicator polypeptides is β-gal.

8. The method of claim 1, wherein said first and second fusion constructs are encoded by a nucleic acid segment under the control of a promoter operable in said prokaryotic host cell.

9. The method of claim 1, wherein said target peptide and LEP bind with an affinity in the range of about $10^{-3}$ to about $10^{-6}$ M.

10. The method of claim 9, wherein said target peptide and LEP bind with an affinity in the range of about $10^{-4}$ M.

11. The method of claim 9, wherein said target peptide and LEP bind with an affinity in the range of about $10^{-5}$ M.

12. The method of claim 9, wherein said target peptide and LEP bind with an affinity in the range of about $10^{-6}$ M.

13. The method of claim 1, further comprising random mutagenesis of said LEP, followed by measuring the change, if any, in the binding affinity of said LEP for said target.

14. The method of claim 13, wherein said measuring comprises effecting binding of said LEP to said target peptide under conditions more stringent than in claim 1.

15. The method of claim 1, further comprising:
   (e) linking said identified LEP to a third peptide, whereby said linking permits said identified LEP and said third peptide to interact independently with said target peptide;
   (f) then contacting said target peptide with the identified LEP-third peptide complex, and (g) followed by determining the change, if any, in the binding affinity of said LEP for said target peptide.

16. The method of claim 15, wherein said measuring comprises effecting binding of said LEP to said target peptide under conditions more stringent than in claim 1.

17. The method of claim 15, wherein said third peptide is known to bind said target peptide.

18. The method of claim 15, wherein said third peptide is a member of a peptide or peptidomimetic library.

19. The method of claim 1, wherein said target peptide is an enzyme substrate, an antigen, or a eukaryotic cell antigen.

20. The method of claim 19, wherein said target peptide is an enzyme substrate.

21. The method of claim 20, wherein said enzyme substrate is bacterial, viral or fungal antigen.

22. The method of claim 19, wherein said target peptide is a eukaryotic cell antigen.

23. The method of claim 22, wherein said eukaryotic cell antigen is a tumor cell marker, an HLA antigen, a cell surface receptor, or a cell surface transporter.

24. The method of claim 1, further comprising, prior to said determining, the step of stabilizing the interaction between said target peptide and said LEP.

25. The method of claim 24, wherein said stabilizing is achieved via cross-linking or phototrapping.

26. The method of claim 1, wherein said first peptide comprises a multimer of a smaller peptide unit.

27. The method of claim 1, further comprising assessing binding of said target peptide to said identified LEP by Western blot, mass spectroscopy, or nuclear magnetic resonance.

\* \* \* \* \*